(12) United States Patent
Shapiro et al.

(10) Patent No.: US 11,666,663 B2
(45) Date of Patent: Jun. 6, 2023

(54) HEXAMERIC TETRAHEDRAL RNA NANOSTRUCTURES

(71) Applicants: The United States of America, as represented by the Secretary, Department of Health and Human Services, Bethesda, MD (US); The Regents of the University of California, Oakland, CA (US)

(72) Inventors: Bruce A. Shapiro, Gaithersburg, MD (US); Paul J. Zakrevsky, Frederick, MD (US); Luc Jaeger, Goleta, CA (US)

(73) Assignees: The United States of America, as represented by the Secretary, Department of Health and Human Services, Bethesda, MD (US); The Regents of the University of California, Oakland, CA (US)

( * ) Notice: Subject to any disclaimer, the term of this patent is extended or adjusted under 35 U.S.C. 154(b) by 25 days.

(21) Appl. No.: 17/053,615

(22) PCT Filed: May 8, 2019

(86) PCT No.: PCT/US2019/031356
§ 371 (c)(1),
(2) Date: Nov. 6, 2020

(87) PCT Pub. No.: WO2019/217576
PCT Pub. Date: Nov. 14, 2019

(65) Prior Publication Data
US 2021/0069345 A1 Mar. 11, 2021

Related U.S. Application Data

(60) Provisional application No. 62/696,619, filed on Jul. 11, 2018, provisional application No. 62/668,653, filed on May 8, 2018.

(51) Int. Cl.
C12N 15/113 (2010.01)
A61K 47/54 (2017.01)
(Continued)

(52) U.S. Cl.
CPC ........ A61K 47/6929 (2017.08); A61K 47/549 (2017.08); B82Y 5/00 (2013.01);
(Continued)

(58) Field of Classification Search
CPC ............ A61K 47/6929; C12N 2320/32; C12N 15/113; C12N 15/1137; B82Y 5/00
See application file for complete search history.

(56) References Cited

U.S. PATENT DOCUMENTS 9,732,337 B2  8/2017  Shapiro et al.

FOREIGN PATENT DOCUMENTS

WO  WO 2008/039254 A2  4/2008
WO  WO 2010/148085 A1  12/2010
(Continued)

OTHER PUBLICATIONS

Afonin, et al., "In vitro Assembly of Cubic RNA-Based Scaffolds Designed in silico," Nat Nanotechnology 5(9): 676-682 (Sep. 2010) Author Manuscript.
(Continued)

Primary Examiner — Terra C Gibbs
(74) Attorney, Agent, or Firm — Leydig, Voit & Mayer

(57) ABSTRACT

Disclosed are nanostructures comprising a ribonucleic acid (RNA) scaffold comprising a hexameric tetrahedral core. The tetrahedral core may comprise four hexameric RNA nanorings linked together. Related pharmaceutical compositions, methods of modulating the expression of a target gene in a mammal, methods of treating or preventing a
(Continued)

disease in a mammal, and methods of producing a hexameric tetrahedral RNA nanostructure are also disclosed.

24 Claims, 17 Drawing Sheets

Specification includes a Sequence Listing.

(51) Int. Cl.
    *A61K 47/69*         (2017.01)
    *B82Y 5/00*          (2011.01)
(52) U.S. Cl.
    CPC ........ *C12N 15/113* (2013.01); *C12N 15/1137* (2013.01); *C12N 2310/14* (2013.01)

(56) References Cited

FOREIGN PATENT DOCUMENTS

| | | |
|---|---|---|
| WO | WO 2012/125987 A2 | 9/2012 |
| WO | WO 2015/042101 A1 | 3/2015 |
| WO | WO 2015/171827 A1 | 11/2015 |
| WO | WO 2017/189870 A1 | 11/2017 |
| WO | WO 2017/197009 A1 | 11/2017 |

OTHER PUBLICATIONS

Afonin, et al., "Design and self-assembly of siRNA-functionalized RNA nanoparticles for use in automated nanomedicine," *Nat Protoc* 6(12): 2022-2034 (Dec. 2011) Author Manuscript.
Afonin, et al., "Multifunctional RNA Nanoparticles," *Nano Letters* 14: 5662-5671 (Sep. 2014).
Badu, et al., "Modeling of RNA nanotubes using molecular dynamics simulation," *European Biophysics Journal* 43: 555-564 (Nov. 2014).
European Patent Office, International Search Report, European Patent Office PCT/US2019/031356, dated Jul. 17, 2019, 10 pages.
European Patent Office, Written Opinion of the International Searching Authority, European Patent Office PCT/US2019/031356, dated Jul. 17, 2019, 5 pages.
Grabow, et al., "Self-Assembling RNA Nanorings Based on RNAI/II Inverse Kissing Complexes," *Nano Letters* 11(2): 878-887 (Feb. 2011) Author Manuscript.
Grabow, et al., "RNA modularity for synthetic biology," *F1000 Prime Reports* 5:46 (Nov. 2013).
Guo, et al., "Size, Shape, and Sequence-Dependent Immunogenicity of RNA Nanoparticles," *Molecular Therapy Nuclei Acids* 9: 399-408 (Dec. 2017).
Hendrix, et al., "RNA structural motifs: building blocks of a modular biomolecule," *Quarterly Reviews of Biophysics* 38(3): 221-243 (Aug. 2005).
International Bureau of WIPO, International Preliminary Report on Patentability, PCT/US2019/031356 dated Nov. 20, 2020, 7 pages.
Jaeger, et al., "TectoRNA: modular assembly units for the construction of RNA nano-objects," *Nuclei Acids Research* 29(2): 455-463 (Jan. 2001).
Jaeger, et al., "The UA handle: a Versatile Submotif in Stable RNA Architectures," *Nucleic Acids Research* 37(1): 215-230 (2009) published online Nov. 26, 2008.
Jasinski, et al., "Advancement of the Emerging Field of RNA Nanotechnology," *ACS Nano* 11: 1142-1164 (Jan. 2017).
Khisamutdinov, et al., "Fabrication of RNA 3D Nanoprism for Loading and Protection of Small RNAs and Model Drugs," *Adv Mater* 28(45): 10079-10087 (Dec. 2016) Author Manuscript.
Lee, et al., "The Solution structure of an RNA loop-loop complex: the ColE1 inverted loop sequence," *Structure* 6(8): 993-1007 (Aug. 1998).
Lee, et al., "Molecularly Self-Assembled Nucleic Acid Nanoparticles for Targeted In Vivo siRNA Delivery," *Nat Nanotechnol* 7(6): 389-393 (Jun. 2012) Author Manuscript.
Leontis, et al., "The building blocks and motifs of RNA architecture," *Curr Opin Struc Biol.* 16(3): 279-287 (Jun. 2006) Author Manuscript.
Li, et al., "Controllable Self-assembly of RNA Tetrahedrons with Precise Shape and Size for Cancer Targeting," *Adv Mater.* 28(34): 7501-7507 (Sep. 2016) Author Manuscript.
Lyubchenko, et al., "Imaging of Nucleic Acids with Atomic Force Microscopy," *Methods* 54(2): 274-283 (Jun. 2011) Author Manuscript.
Noller, "RNA Structure: Reading the Ribosome," *Science* 309: 1508-1514 (Sep. 2005).
Patel, "RNAi Nanotechnology: A Platform for siRNA Screening and Cancer Gene Therapy," Seton Hall University Dissertations and Theses (ETDs) South Orange, New Jersey, USA (Aug. 2016) 162 pages.
Shapiro "Simultaneous Targeting of Gene Expression Pathways using RNA-based Nanoconstructs," retrieved from: https://binkley2.ncifcrf.gov/~bshapiro/ Mid-Atlantic DNA Nanotechnology Symposium, Gaithersburg, Maryland USA (Dec. 8, 2017) 50 pages.
Shu, et al., "Fabrication of 14 different RNA nanoparticles for specific tumor targeting without accumulation in normal organs," *RNA* 19: 767-777 (Jun. 2013).
Xu, et al., "Delivery systems for siRNA drug development in cancer therapy," *Asian Journal of Pharmaceutical Sciences* 10: 1-12 (Feb. 2015).
Yingling, et al., "Computational Design of an RNA Hexagonal Nanoring and an RNA Nanotube," *Nano Letters* 7(8): 2328-2334 (Aug. 2007).
Zakrevsky, et al., "Design and Characterization of Three-Dimensional RNA Tetrahedrons for Therapeutic Application," NIH Poster, CCR RNA Biology Workshop, Rockville, Maryland USA(Dec. 1, 2017) 1 page.
Zakrevsky, "Development of Therapeutic, Self-Assembling RNA Nanoparticles Inspired by the ColE1 Kissing Complex," PowerPoint and Oral presentation, CCR FYI Seiminar Series, National Cancer Institute, Frederick, Maryland USA (Mar. 7, 2018) 65 pages.
"Truncated tetrahedron," wikipedia.org/wiki/Truncated_tetrahedron, printed Aug. 11, 2022.
"Truncated tetrahedron," mathworld.wolfram.com/TruncatedTetrahedron.html, printed Aug. 11, 2022.
Zakrevsky et al., "Truncated tetrahedral RNA nanostructures exhibit enhanced features for delivery of RNAi substrates", *Nanoscale*, vol. 12, pp. 2555-2568 (2020).

+1 bp shift

Ideal geometry

-1 bp shift

2, 2, 1, 1 Distribution

 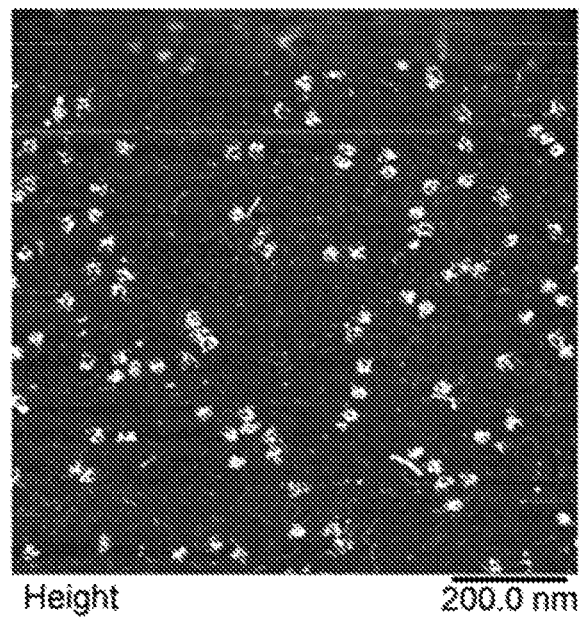
FIG. 4A  FIG. 4B
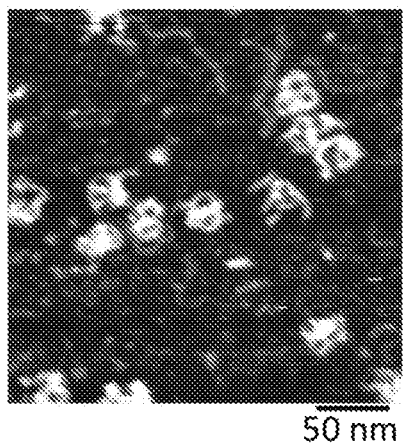 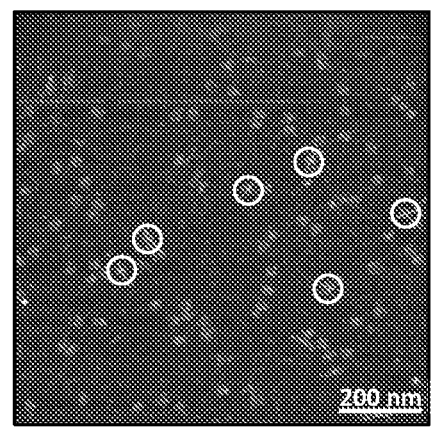
FIG. 4C  FIG. 4D

SEQUENCE LISTING

```
<160> NUMBER OF SEQ ID NOS: 55

<210> SEQ ID NO 1
<211> LENGTH: 44
<212> TYPE: RNA
<213> ORGANISM: Artificial Sequence
<220> FEATURE:
<223> OTHER INFORMATION: synthetic

<400> SEQUENCE: 1
gggaauccgu ccacuggauu cccgucacag agccugccug ugac                    44

<210> SEQ ID NO 2
<211> LENGTH: 44
<212> TYPE: RNA
<213> ORGANISM: Artificial Sequence
<220> FEATURE:
<223> OTHER INFORMATION: synthetic

<400> SEQUENCE: 2
gggaauccgc aggcuggauu cccgucacag agaacgccug ugac                    44

<210> SEQ ID NO 3
<211> LENGTH: 44
<212> TYPE: RNA
<213> ORGANISM: Artificial Sequence
<220> FEATURE:
<223> OTHER INFORMATION: synthetic

<400> SEQUENCE: 3
gggaauccgc guucuggauu cccgucacag acgucuccug ugac                    44

<210> SEQ ID NO 4
<211> LENGTH: 44
<212> TYPE: RNA
<213> ORGANISM: Artificial Sequence
<220> FEATURE:
<223> OTHER INFORMATION: synthetic

<400> SEQUENCE: 4
gggaauccga gacguggauu cccgucacag ucguggucug ugac                    44
```

```
<210> SEQ ID NO 5
<211> LENGTH: 44
<212> TYPE: RNA
<213> ORGANISM: Artificial Sequence
<220> FEATURE:
<223> OTHER INFORMATION: synthetic

<400> SEQUENCE: 5
gggaauccac cacgaggauu cccgucacag aaccauccug ugac         44

<210> SEQ ID NO 6
<211> LENGTH: 44
<212> TYPE: RNA
<213> ORGANISM: Artificial Sequence
<220> FEATURE:
<223> OTHER INFORMATION: synthetic

<400> SEQUENCE: 6
gggaauccga ugguuggauu cccgucacag aguggaccug ugac         44

<210> SEQ ID NO 7
<211> LENGTH: 73
<212> TYPE: RNA
<213> ORGANISM: Artificial Sequence
<220> FEATURE:
<223> OTHER INFORMATION: synthetic

<400> SEQUENCE: 7
gggaaccguc cacugguucc cgcuacgaga gccugccucg uagcuucggu ggugcagaug    60
aacuucaggg uca                                                      73

<210> SEQ ID NO 8
<211> LENGTH: 73
<212> TYPE: RNA
<213> ORGANISM: Artificial Sequence
<220> FEATURE:
<223> OTHER INFORMATION: synthetic

<400> SEQUENCE: 8
gggaaccgca ggcugguucc cgcuacgaga gaacgccucg uagcuucggu ggugcagaug    60
aacuucaggg uca                                                      73

<210> SEQ ID NO 9
<211> LENGTH: 73
<212> TYPE: RNA
<213> ORGANISM: Artificial Sequence
<220> FEATURE:
<223> OTHER INFORMATION: synthetic

<400> SEQUENCE: 9
gggaaccgcg uucugguucc cgcuacgaga cgucuccucg uagcuucggu ggugcagaug    60
aacuucaggg uca                                                      73

<210> SEQ ID NO 10
<211> LENGTH: 73
<212> TYPE: RNA
<213> ORGANISM: Artificial Sequence
<220> FEATURE:
<223> OTHER INFORMATION: synthetic

<400> SEQUENCE: 10
gggaaccgag acgugguucc cgcuacgagu cguggucucg uagcuucggu ggugcagaug    60
```
aacuucaggg uca                                                           73

<210> SEQ ID NO 11
<211> LENGTH: 73
<212> TYPE: RNA
<213> ORGANISM: Artificial Sequence
<220> FEATURE:
<223> OTHER INFORMATION: synthetic

<400> SEQUENCE: 11
gggaaccacc acgagguucc cgcuacgaga accauccucg uagcuucggu ggugcagaug         60
aacuucaggg uca                                                           73

<210> SEQ ID NO 12
<211> LENGTH: 73
<212> TYPE: RNA
<213> ORGANISM: Artificial Sequence
<220> FEATURE:
<223> OTHER INFORMATION: synthetic

<400> SEQUENCE: 12
gggaaccgau gguugguucc cgcuacgaga guggaccucg uagcuucggu ggugcagaug         60
aacuucaggg uca                                                           73

<210> SEQ ID NO 13
<211> LENGTH: 73
<212> TYPE: RNA
<213> ORGANISM: Artificial Sequence
<220> FEATURE:
<223> OTHER INFORMATION: synthetic

<400> SEQUENCE: 13
gggaaccgca ggcugguucc cgcuacgaga gaacgccucg uagcuuauac gcguauuaua         60
cgcgauuaac gac                                                           73

<210> SEQ ID NO 14
<211> LENGTH: 73
<212> TYPE: RNA
<213> ORGANISM: Artificial Sequence
<220> FEATURE:
<223> OTHER INFORMATION: synthetic

<400> SEQUENCE: 14
gggaaccgag acgugguucc cgcuacgagu cguggucucg uagcuuauac gcguauuaua         60
cgcgauuaac gac                                                           73

<210> SEQ ID NO 15
<211> LENGTH: 73
<212> TYPE: RNA
<213> ORGANISM: Artificial Sequence
<220> FEATURE:
<223> OTHER INFORMATION: synthetic

<400> SEQUENCE: 15
gggaaccacc acgagguucc cgcuacgaga accauccucg uagcuuauac gcguauuaua         60
cgcgauuaac gac                                                           73

<210> SEQ ID NO 16
<211> LENGTH: 73
<212> TYPE: RNA
<213> ORGANISM: Artificial Sequence
<220> FEATURE:
<223> OTHER INFORMATION: synthetic

<400> SEQUENCE: 16
gggaaccgau gguugguucc cgcuacgaga guggaccucg uagcuuauac gcguauuaua    60
cgcgauuaac gac                                                       73

<210> SEQ ID NO 17
<211> LENGTH: 73
<212> TYPE: RNA
<213> ORGANISM: Artificial Sequence
<220> FEATURE:
<223> OTHER INFORMATION: synthetic

<400> SEQUENCE: 17
gggaaccguc cacugguucc cgcuacgaga gccugccucg uagcuuucgu cauuaagcag    60
cucguuaaug guu                                                       73

<210> SEQ ID NO 18
<211> LENGTH: 73
<212> TYPE: RNA
<213> ORGANISM: Artificial Sequence
<220> FEATURE:
<223> OTHER INFORMATION: synthetic

<400> SEQUENCE: 18
gggaaccgca ggcugguucc cgcuacgaga gaacgccucg uagcuuucgu cauuaagcag    60
cucguuaaug guu                                                       73

<210> SEQ ID NO 19
<211> LENGTH: 73
<212> TYPE: RNA
<213> ORGANISM: Artificial Sequence
<220> FEATURE:
<223> OTHER INFORMATION: synthetic

<400> SEQUENCE: 19
gggaaccgcg uucugguucc cgcuacgaga cgucccucg uagcuuucgu cauuaagcag     60
cucguuaaug guu                                                       73

<210> SEQ ID NO 20
<211> LENGTH: 73
<212> TYPE: RNA
<213> ORGANISM: Artificial Sequence
<220> FEATURE:
<223> OTHER INFORMATION: synthetic

<400> SEQUENCE: 20
gggaaccgag acgugguucc cgcuacgagu cguggucucg uagcuuucgu cauuaagcag    60
cucguuaaug guu                                                       73

<210> SEQ ID NO 21
<211> LENGTH: 73
<212> TYPE: RNA
<213> ORGANISM: Artificial Sequence
<220> FEATURE:
<223> OTHER INFORMATION: synthetic

<400> SEQUENCE: 21
gggaaccacc acgagguucc cgcuacgaga accauccucg uagcuuucgu cauuaagcag    60
cucguuaaug guu                                                       73

<210> SEQ ID NO 22

```
<211> LENGTH: 73
<212> TYPE: RNA
<213> ORGANISM: Artificial Sequence
<220> FEATURE:
<223> OTHER INFORMATION: synthetic

<400> SEQUENCE: 22
gggaaccgau ggsuugguucc cgcuacgaga guggaccucg uagcuuucgu cauuaagcag    60
cucguuaaug guu                                                        73

<210> SEQ ID NO 23
<211> LENGTH: 102
<212> TYPE: RNA
<213> ORGANISM: Artificial Sequence
<220> FEATURE:
<223> OTHER INFORMATION: synthetic

<400> SEQUENCE: 23
gguguccacu acccucgaca gaaucugaca ucagccugcg augucuaaga cagguccac     60 ucaugucgac agauucugca cagagccugc cugugcuaag ag                       102

<210> SEQ ID NO 24
<211> LENGTH: 102
<212> TYPE: RNA
<213> ORGANISM: Artificial Sequence
<220> FEATURE:
<223> OTHER INFORMATION: synthetic

<400> SEQUENCE: 24
ggugcguucu acccucgaca gaaucugaca ucacgucucg augucuaaga cauggcguuc    60
ucaugucgac agauucugca cagacgucuc cugugcuaag ag                       102

<210> SEQ ID NO 25
<211> LENGTH: 102
<212> TYPE: RNA
<213> ORGANISM: Artificial Sequence
<220> FEATURE:
<223> OTHER INFORMATION: synthetic

<400> SEQUENCE: 25
gggaccacga cccgcugaca gaaucugaca ucaaccaucg augucuaaga caugaccacg    60
acaugucgac agauucugca cagaaccauc cugugcuaaa gc                       102

<210> SEQ ID NO 26
<211> LENGTH: 52
<212> TYPE: RNA
<213> ORGANISM: Artificial Sequence
<220> FEATURE:
<223> OTHER INFORMATION: synthetic

<400> SEQUENCE: 26
ggcaacuuug aucccucggu uuagcgccgg ccuuuucucc cacacuuuca cg             52

<210> SEQ ID NO 27
<211> LENGTH: 52
<212> TYPE: RNA
<213> ORGANISM: Artificial Sequence
<220> FEATURE:
<223> OTHER INFORMATION: synthetic

<400> SEQUENCE: 27
gggaaauuuc guguagguu uuguugcccg uguucuacg auuacuuugg uc               52
```

<210> SEQ ID NO 28
<211> LENGTH: 52
<212> TYPE: RNA
<213> ORGANISM: Artificial Sequence
<220> FEATURE:
<223> OTHER INFORMATION: synthetic

<400> SEQUENCE: 28 ggcauuuuc gagacagcau uuuucccga ccuuugcgga uuguauuuua gg         52

<210> SEQ ID NO 29
<211> LENGTH: 52
<212> TYPE: RNA
<213> ORGANISM: Artificial Sequence
<220> FEATURE:
<223> OTHER INFORMATION: synthetic

<400> SEQUENCE: 29
ggcgcuuuug accuucugcu uuaugucccc uauuucuuaa ugacuuugg cc         52

<210> SEQ ID NO 30
<211> LENGTH: 52
<212> TYPE: RNA
<213> ORGANISM: Artificial Sequence
<220> FEATURE:
<223> OTHER INFORMATION: synthetic

<400> SEQUENCE: 30
gggagauuua gucauuaagu uuuacaaucc gcuuuguaau cguaguuugu gu         52

<210> SEQ ID NO 31
<211> LENGTH: 52
<212> TYPE: RNA
<213> ORGANISM: Artificial Sequence
<220> FEATURE:
<223> OTHER INFORMATION: synthetic

<400> SEQUENCE: 31
gggaucuuua ccuaccacgu uuugcugucu cguuugcaga aggucuuucc ga         52

<210> SEQ ID NO 32
<211> LENGTH: 81
<212> TYPE: RNA
<213> ORGANISM: Artificial Sequence
<220> FEATURE:
<223> OTHER INFORMATION: synthetic

<400> SEQUENCE: 32
ggcaacuuug aucccucggu uuagcgccgg ccuuucucc cacacuuuca cguucggugg    60
ugcagaugaa cuucaggguc a                                           81

<210> SEQ ID NO 33
<211> LENGTH: 81
<212> TYPE: RNA
<213> ORGANISM: Artificial Sequence
<220> FEATURE:
<223> OTHER INFORMATION: synthetic

<400> SEQUENCE: 33
gggaaauuuc gugguagguu uuguugcccg uguuucuacg auuacuuugg ucuucggugg    60
ugcagaugaa cuucaggguc a                                           81

<210> SEQ ID NO 34
<211> LENGTH: 81
<212> TYPE: RNA

```
<213> ORGANISM: Artificial Sequence
<220> FEATURE:
<223> OTHER INFORMATION: synthetic

<400> SEQUENCE: 34
ggacauuuuc gagacagcau uuuucccga ccuuugcgga uuguauuuua gguucggugg    60
ugcagaugaa cuucagggtc a                                            81

<210> SEQ ID NO 35
<211> LENGTH: 81
<212> TYPE: RNA
<213> ORGANISM: Artificial Sequence
<220> FEATURE:
<223> OTHER INFORMATION: synthetic

<400> SEQUENCE: 35
ggcgcuuuug accuucugcu uuaugucccc uauuucuuaa ugacuuugg ccucggugg     60 ugcagaugaa cuucagggtc a                                            81

<210> SEQ ID NO 36
<211> LENGTH: 81
<212> TYPE: RNA
<213> ORGANISM: Artificial Sequence
<220> FEATURE:
<223> OTHER INFORMATION: synthetic

<400> SEQUENCE: 36
gggagauuua gucauuaagu uuuacaaucc gcuuuguaau cguaguuugu guuucggugg   60
ugcagaugaa cuucagggtc a                                            81

<210> SEQ ID NO 37
<211> LENGTH: 81
<212> TYPE: RNA
<213> ORGANISM: Artificial Sequence
<220> FEATURE:
<223> OTHER INFORMATION: synthetic

<400> SEQUENCE: 37
gggaucuuua ccuaccacgu uuugcugucu cguuugcaga aggucuuucc gauucggugg   60
ugcagaugaa cuucagggtc a                                            81

<210> SEQ ID NO 38
<211> LENGTH: 81
<212> TYPE: RNA
<213> ORGANISM: Artificial Sequence
<220> FEATURE:
<223> OTHER INFORMATION: synthetic

<400> SEQUENCE: 38
gggagauuua gucauuaagu uuuacaaucc gcuuuguaau cguaguuugu guuuauacgc   60
guauuauacg cgauuaacga c                                            81

<210> SEQ ID NO 39
<211> LENGTH: 81
<212> TYPE: RNA
<213> ORGANISM: Artificial Sequence
<220> FEATURE:
<223> OTHER INFORMATION: synthetic

<400> SEQUENCE: 39
gggaucuuua ccuaccacgu uuugcugucu cguuugcaga aggucuuucc gauuauacgc   60
guauuauacg cgauuaacga c                                            81
```

<210> SEQ ID NO 40
<211> LENGTH: 81
<212> TYPE: RNA
<213> ORGANISM: Artificial Sequence
<220> FEATURE:
<223> OTHER INFORMATION: synthetic

<400> SEQUENCE: 40
ggcaacuuug aucccucggu uuagcgccgg ccuuucucc cacacuuuca cguuucguca    60
uuaagcagcu cguuaauggu u                                             81

<210> SEQ ID NO 41
<211> LENGTH: 81
<212> TYPE: RNA
<213> ORGANISM: Artificial Sequence
<220> FEATURE:
<223> OTHER INFORMATION: synthetic

<400> SEQUENCE: 41
gggaaauuuc gugguagguu uguugcccg uguuucuacg auuacuuugg ucuuucguca    60
uuaagcagcu cguuaauggu u                                             81

<210> SEQ ID NO 42
<211> LENGTH: 81
<212> TYPE: RNA
<213> ORGANISM: Artificial Sequence
<220> FEATURE:
<223> OTHER INFORMATION: synthetic

<400> SEQUENCE: 42
ggacauuuuc gagacagcau uuuucccga ccuugcgga uguauuuua gguuucguca      60 uuaagcagcu cguuaauggu u                                             81

<210> SEQ ID NO 43
<211> LENGTH: 81
<212> TYPE: RNA
<213> ORGANISM: Artificial Sequence
<220> FEATURE:
<223> OTHER INFORMATION: synthetic

<400> SEQUENCE: 43
ggcgcuuuug accuucugcu uuaugucccc uauuucuuaa ugacuuugg ccuuucguca    60 uuaagcagcu cguuaauggu u                                             81

<210> SEQ ID NO 44
<211> LENGTH: 81
<212> TYPE: RNA
<213> ORGANISM: Artificial Sequence
<220> FEATURE:
<223> OTHER INFORMATION: synthetic

<400> SEQUENCE: 44
gggagauuua gucauuaagu uuuacaaucc gcuuuguaau cguaguuugu guuucguca    60 uuaagcagcu cguuaauggu u                                             81

<210> SEQ ID NO 45
<211> LENGTH: 81
<212> TYPE: RNA
<213> ORGANISM: Artificial Sequence
<220> FEATURE:
<223> OTHER INFORMATION: synthetic

<400> SEQUENCE: 45
gggaucuuua ccuaccacgu uuugcugucu cguuugcaga aggucuuucc gauucggugg    60
ugcagaugaa cuucaggguc a                                             81

<210> SEQ ID NO 46
<211> LENGTH: 25
<212> TYPE: RNA
<213> ORGANISM: Artificial Sequence
<220> FEATURE:
<223> OTHER INFORMATION: synthetic
<220> FEATURE:
<221> NAME/KEY: miscellaneous
<222> LOCATION: (1)..(1)
<223> OTHER INFORMATION: Adenine at position 1 comprises 5'
      monophosphate

<400> SEQUENCE: 46
acccugaagu ucaucugcac caccg                                         25

<210> SEQ ID NO 47
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: miscellaneous
<222> LOCATION: (1)..(1)
<223> OTHER INFORMATION: Wherein deoxyadenine at position 1 comprises
      6-carboxyfluorescein
<220> FEATURE:
<221> NAME/KEY: miscellaneous
<222> LOCATION: (1)..(25)
<223> OTHER INFORMATION: Wherein each nucleotide is a deoxynucleotide

<400> SEQUENCE: 47
accctgaagt tcatctgcac caccg                                         25

<210> SEQ ID NO 48
<211> LENGTH: 25
<212> TYPE: RNA
<213> ORGANISM: Artificial Sequence
<220> FEATURE:
<223> OTHER INFORMATION: synthetic
<220> FEATURE:
<221> NAME/KEY: miscellaneous
<222> LOCATION: (1)..(1)
<223> OTHER INFORMATION: Cytosine at position 1 comprises 5'
      monophosphate

<400> SEQUENCE: 48
cguuaaucgc guauaauacg cguau                                         25

<210> SEQ ID NO 49
<211> LENGTH: 25
<212> TYPE: RNA
<213> ORGANISM: Artificial Sequence
<220> FEATURE:
<223> OTHER INFORMATION: synthetic
<220> FEATURE:
<221> NAME/KEY: miscellaneous
<222> LOCATION: (1)..(1)
<223> OTHER INFORMATION: Cytosine at position 1 comprises 5'
      monophosphate

<400> SEQUENCE: 49
ccauuaacga gcugcuuaau gacga                                         25

<210> SEQ ID NO 50
<211> LENGTH: 73
<212> TYPE: RNA
<213> ORGANISM: Artificial Sequence
<220> FEATURE:
<223> OTHER INFORMATION: synthetic

<400> SEQUENCE: 50
gggaauccgc aggcuggauu cccgucacag agaacgccug ugacuugaug cgcguagucc    60
guauggcuaa gag                                                      73

<210> SEQ ID NO 51
<211> LENGTH: 73
<212> TYPE: RNA
<213> ORGANISM: Artificial Sequence
<220> FEATURE:
<223> OTHER INFORMATION: synthetic

<400> SEQUENCE: 51
gggaauccga gacguggauu cccgucacag ucguggucug ugacuugaug cgcguagucc    60
guauggcuaa gag                                                      73

<210> SEQ ID NO 52
<211> LENGTH: 73
<212> TYPE: RNA
<213> ORGANISM: Artificial Sequence
<220> FEATURE:
<223> OTHER INFORMATION: synthetic

<400> SEQUENCE: 52
gggaauccga ugguuggauu cccgucacag aguggaccug ugacuugaug cgcguagucc    60
guauggcuaa gag                                                      73

<210> SEQ ID NO 53
<211> LENGTH: 73
<212> TYPE: RNA
<213> ORGANISM: Artificial Sequence
<220> FEATURE:
<223> OTHER INFORMATION: synthetic

<400> SEQUENCE: 53
gggaauccgc aggcuggauu cccgucacag agaacgccug ugacuugcuu ccgggugcaa    60
uggaagguga uac                                                      73

<210> SEQ ID NO 54
<211> LENGTH: 73
<212> TYPE: RNA
<213> ORGANISM: Artificial Sequence
<220> FEATURE:
<223> OTHER INFORMATION: synthetic

<400> SEQUENCE: 54
gggaauccga gacguggauu cccgucacag ucguggucug ugacuugcuu ccgggugcaa    60
uggaagguga uac                                                      73

<210> SEQ ID NO 55
<211> LENGTH: 73
<212> TYPE: RNA
<213> ORGANISM: Artificial Sequence
<220> FEATURE:
<223> OTHER INFORMATION: synthetic

<400> SEQUENCE: 55

```
gggaauccga ugguuggauu cccgucacag aguggaccug ugacuugcuu ccgggugcaa        60
uggaagguga uac                                                          73
```

HEXAMERIC TETRAHEDRAL RNA NANOSTRUCTURES

CROSS-REFERENCE TO RELATED APPLICATIONS

This patent application is the U.S. national stage of International Patent Application No. PCT/US2019/031356, filed May 8, 2019, which claims the benefit of U.S. Provisional Patent Applications No. 62/668,653, filed May 8, 2018, and 62/696,619, filed Jul. 11, 2018, all of which are incorporated by reference in their entireties herein.

STATEMENT REGARDING FEDERALLY SPONSORED RESEARCH OR DEVELOPMENT

This invention was made with Government support under project number Z01BC01106109 by the National Institutes of Health, National Cancer Institute and project number R01GM079604 by the National Institutes of Health, National Institute of General Medical Sciences. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 14.054 Byte ASCII (Text) file named "750722_ST25.txt," dated Nov. 4, 2020.

BACKGROUND OF THE INVENTION

RNA nanostructures may be useful for a variety of nanobiological applications. Such applications may include, for example, the delivery of functional moieties, such as ligand binding motifs or gene expression regulators. Despite advancements in the field of RNA nanostructures, a variety of challenges to the successful application of RNA nanostructures remain. For example, insufficient cellular uptake of the nanostructures may limit the functional (e.g., therapeutic) efficacy of nanostructures carrying functional (e.g., therapeutic) moieties. Accordingly, there exists an unmet need for improved RNA nanostructures.

BRIEF SUMMARY OF THE INVENTION

An embodiment of the invention provides a nanostructure comprising a ribonucleic acid (RNA) scaffold comprising a hexameric tetrahedral core, wherein the tetrahedral core comprises four hexameric RNA nanoring faces linked together.

Another embodiment of the invention provides a nanostructure comprising a ribonucleic acid (RNA) scaffold comprising a hexameric tetrahedral core, wherein the tetrahedral core comprises first, second, third, fourth, fifth, and sixth cross-over monomers; first, second, third, fourth, fifth, sixth, seventh, eighth, ninth, tenth, eleventh, and twelfth dumbbell monomers; wherein the first, second, and third dumbbell monomers and the first, second, and sixth cross-over monomers together form a first hexameric nanoring; wherein the fourth, fifth, and sixth dumbbell monomers and the fourth, fifth, and sixth cross-over monomers together form a second hexameric nanoring; wherein the seventh, eighth, and ninth dumbbell monomers and the first, third, and fifth cross-over monomers together form a third hexameric nanoring; wherein the tenth, eleventh, and twelfth dumbbell monomers and the second, third, and fourth cross-over monomers together form a fourth hexameric nanoring; and wherein each cross-over monomer is shared by two of the hexameric rings to link the hexameric nanorings together to form the hexameric tetrahedral core.

Another embodiment of the invention provides compositions comprising the inventive nanostructure.

Further embodiments of the invention provide methods of modulating the expression of a target gene in a mammal and methods of treating or preventing a disease in a mammal comprising administering the inventive nanostructure or composition to the mammal.

Still another embodiment of the invention provides a method of producing the inventive nanostructure.

BRIEF DESCRIPTION OF THE SEVERAL VIEWS OF THE DRAWING(S)

FIG. 1A is a schematic showing thermal folding and assembly of an RNA nanoring, in an order starting from the unstructured RNA monomer units (top), to the structured dumbbell shaped monomers (middle), and ending with the formed RNA nanoring (bottom). The temperature at which monomers are denatured is 94° C. The letters A, B, C, D, E, and F represent distinct RNA sequences which will form intramolecular contacts at a lower temperature, resulting in the structured dumbbell shaped monomers shown in Step 1. Each monomer unit contains two distinct RNA sequences shown as two different letters from A-F. Step 1: the formation of the structured monomer units, i.e., the formation of the dumbbell shaped monomers, takes place when the RNA monomer units are snap cooled on ice, as shown. The areas of RNA sequences designated as A, B, C, D, E, and F form the circular ends of the dumbbells. As is shown in FIG. 1A, each dumbbell monomer unit has two ends which correspond to a distinct RNA sequence. Step 2, assembly through intermolecular contacts, which takes place at 30° C. in the presence of $Mg^{2+}$, results in the formation of the RNA nanoring. During Step 2, the distinct RNA sequence "dumbbells" will form a loop-loop interaction, also called a kissing complex that mimic the structure and geometry of the inverse ColE1 kissing complex. While individual nanoring assembly requires about 30° C. incubation step, an increased incubation temperature of about 45° C. is preferred for the inventive tetrahedral nanostructures. FIG. 1B is a schematic of a structure of the inverse ColE1 kissing complex (i.e., the ColE1 RNA loop-loop interaction) derived through Nuclear Magnetic Resonance (NMR) studies. This interaction forms a 120° bond between adjacent RNA helices.

FIG. 2A is a schematic of a close-up of a 2-dimensional (planar) UA-handle three-way junction (UAh-3WJ), as it is embedded in each dumbbell monomer, according to an embodiment of the invention.

FIG. 2B is a schematic showing the secondary structure of the 3-dimensional model of the tetrahedral scaffold according to an embodiment of the invention. The secondary structure shows that the 3-dimensional model is made up of four nanorings (labeled 1-4 on the inside of each ring), six H-shaped cross-over monomers, labeled as the numbers 1b, 2b, and 3b on the outside connecting lines, and the numbers 4b, 5b, and 6b, close to the center of the figure), and three dumbbell shaped monomers in each nanoring, labeled as 1a, 2a, and 3a in ring number 1 (top), 4a, 5a, and 6a in ring number 2 (middle), 7a, 8a, and 9a in ring number 3 (bottom left), and 10a, 11a, and 12a in ring number 4 (bottom right).

FIG. 2C is a schematic showing modeling of the positions of the base pairing in the UAh three-way junction and the resulting geometry of the H-shaped monomer. The position of the UAh three-way junction was modeled in various positions in adjacent monomers to find the position that best suited the arrangement of neighboring rings into an ideal tetrahedral geometry by shifting the junction within the dumbbell monomers by one base pair. FIG. 2C shows a +1 base pair shift.

FIG. 2D is a schematic showing modeling of the positions of the base pairing in the UAh three-way junction and the resulting geometry of the H-shaped monomer, according to an embodiment of the invention. The position of the UAh three-way junction was modeled in various positions in adjacent monomers to find the position that best suited the arrangement of neighboring rings into an ideal tetrahedral geometry by shifting the junction within the dumbbell monomers by one base pair. FIG. 2D shows the ideal geometry of the H-shaped monomer.

FIG. 2E is a schematic showing modeling of the positions of the base pairing in the UAh three-way junction and the resulting geometry of the H-shaped monomer. The position of the UAh three-way junction was modeled in various positions in adjacent monomers to find the position that best suited the arrangement of neighboring rings into an ideal tetrahedral geometry by shifting the junction within the dumbbell monomers by one base pair. FIG. 2E shows a −1 base pair shift.

FIG. 4C is an enlarged image of assembled tetrahedral nanostructures characterized by atomic force microscopy, imaged in air, according to an embodiment of the invention. The white shapes are assembled tetrahedral nanostructures. The enlarged image shows the tetrahedral shape of the structures.

FIG. 4D is an image of assembled tetrahedral nanostructures characterized by atomic force microscopy, imaged in air, according to an embodiment of the invention. The white shapes shown are assembled tetrahedral nanostructures. The five circles show areas where cross-sectional measurements of multiple tetrahedral structures were taken. The measurements were used to calculate average particle diameter of the tetrahedral structures.

Figure 4E:
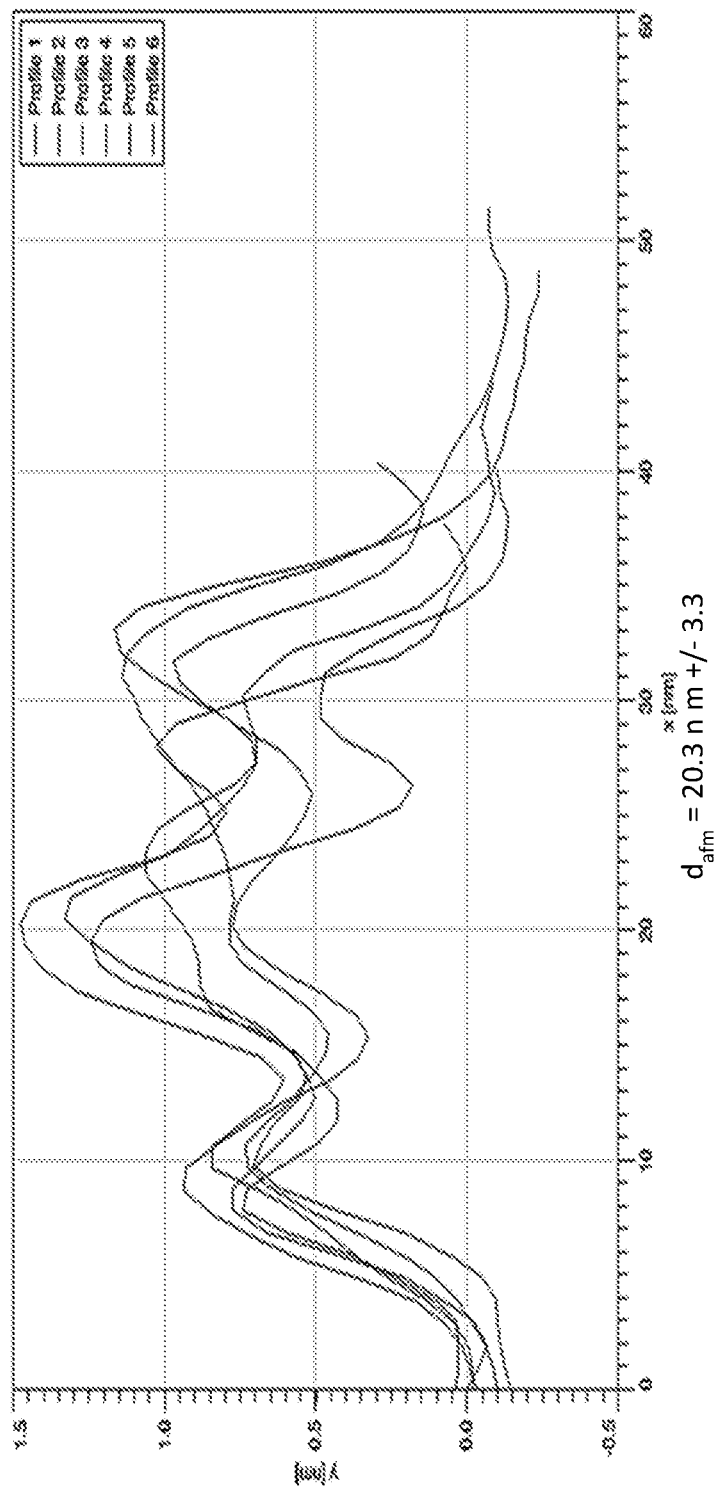
FIG. 4A is the height scale used during atomic force microscopy, in nm, of assembled tetrahedral nanostructures imaged in air, according to an embodiment of the invention.
FIG. 4B is an image of assembled tetrahedral nanostructures characterized by atomic force microscopy, imaged in air, according to an embodiment of the invention. The white shapes shown are assembled tetrahedral nanostructures.

FIG. 4E is a graph of the cross-sectional measurements taken of the white shapes described in the FIG. 4D legend, according to an embodiment of the invention. The average particle diameter ($d_{afm}$) is approximately 20 nm.

Figure 5A:
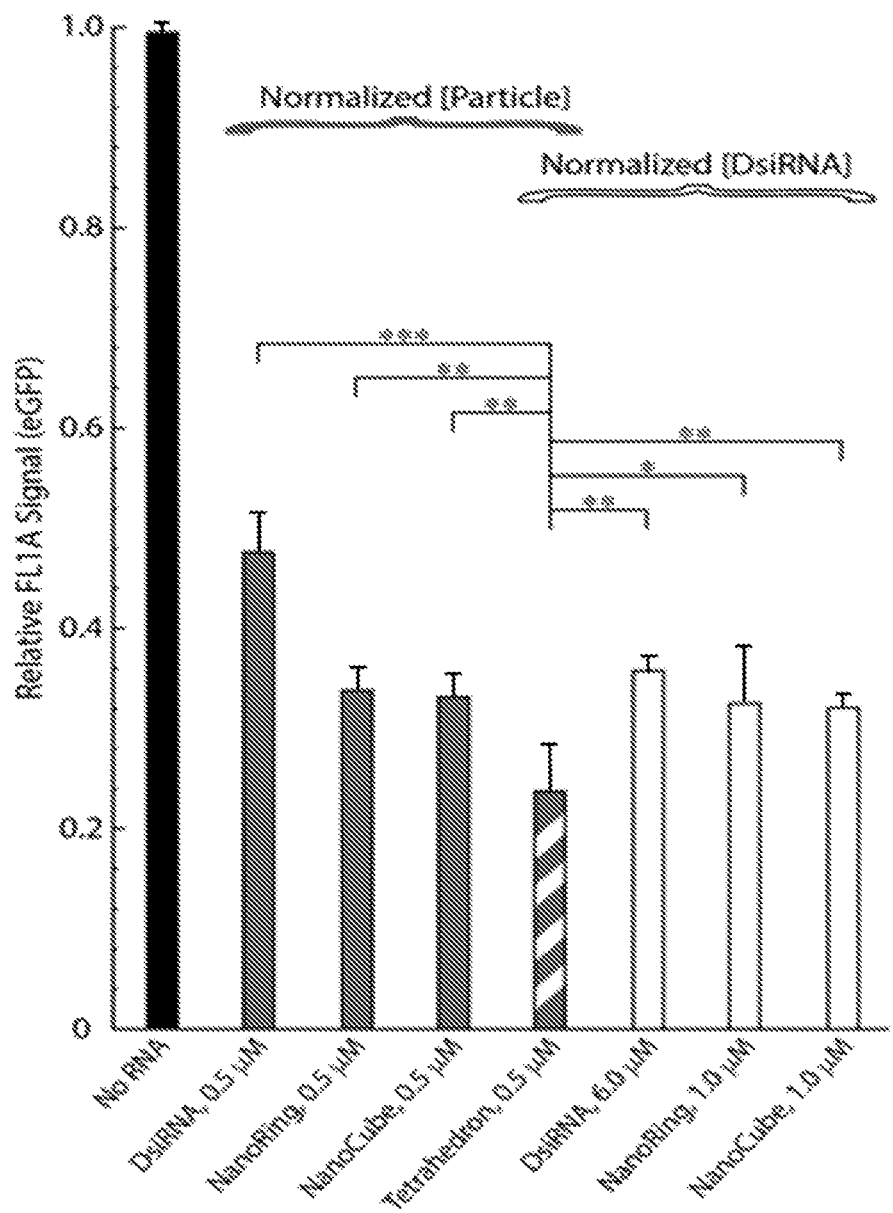

FIG. 5A is a bar graph showing the results of silencing of enhanced green fluorescent protein (eGFP) performed in MDA-MB-231 human breast cancer cells that stably express eGFP. The various nanoparticle shapes, which are listed in the X-axis, with their full complement of DsiRNA arms, were assessed for their ability to knockdown eGFP expression. Transfections were performed at both equimolar concentration of assembled particles and equimolar concentration of available DsiRNAs. Error bars indicate the standard deviation (SD) P-values are *<0.05, <0.01, *<0.001.

Figure 5B:
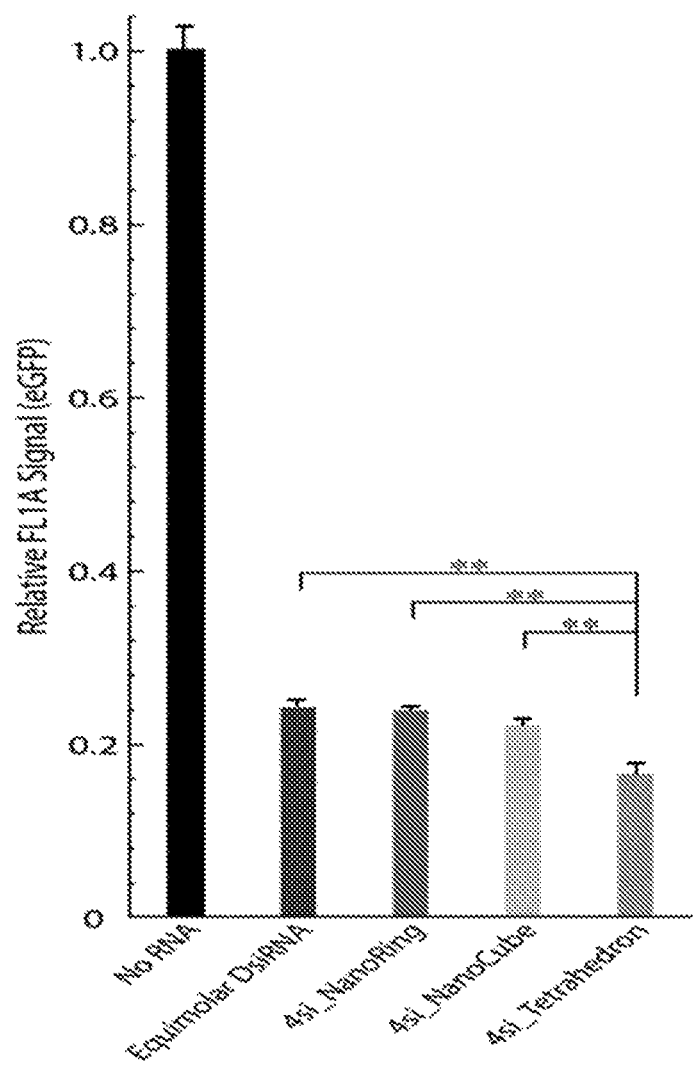

FIG. 5B is a bar graph showing the results of silencing of enhanced green fluorescent protein (eGFP) performed in MDA-MB-231 human breast cancer cells that stably express eGFP. The nanoparticle shapes listed in the X-axis were each assembled with four DsiRNA arms, and assessed for their ability to knockdown eGFP expression. Transfections were performed at both equimolar concentration of assembled particles (and therefore also equimolar concentration of available DsiRNAs). Error bars indicate the standard deviation (SD) P-values are *<0.05, <0.01, *<0.001.

Figure 5C:
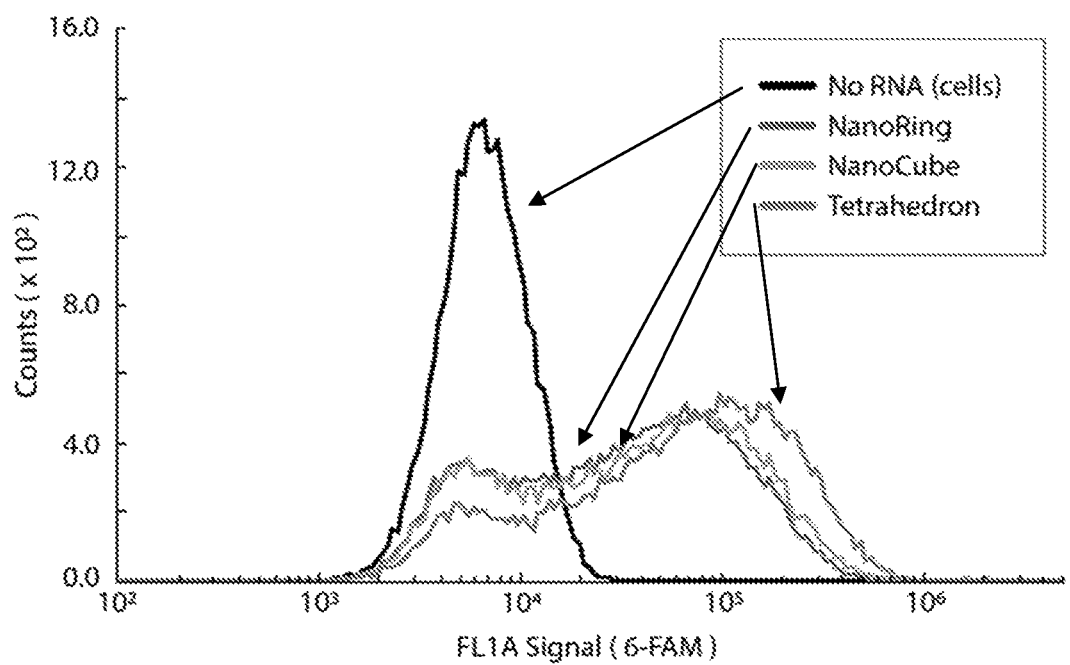

FIG. 5C is a histogram showing the flow cytometry results of cellular uptake studies performed using MDA-MB-231 cells that do not express eGFP. Various RNA particles (shapes are shown in the box) were assembled with their full complement of DsiRNA arms, with four DsiRNA sense strands on each particle fluorescently labeled. Uptake of the fluorescently labeled nanoparticles was determined by flow cytometry.

Figure 5D:
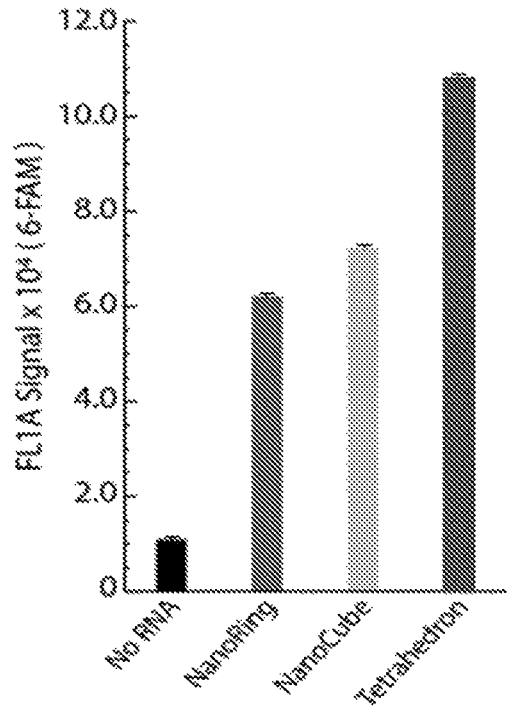

FIG. 5D is a bar graph showing the average fluorescence signal of the various RNA particles described in the FIG. 5C legend.

Figure 6:
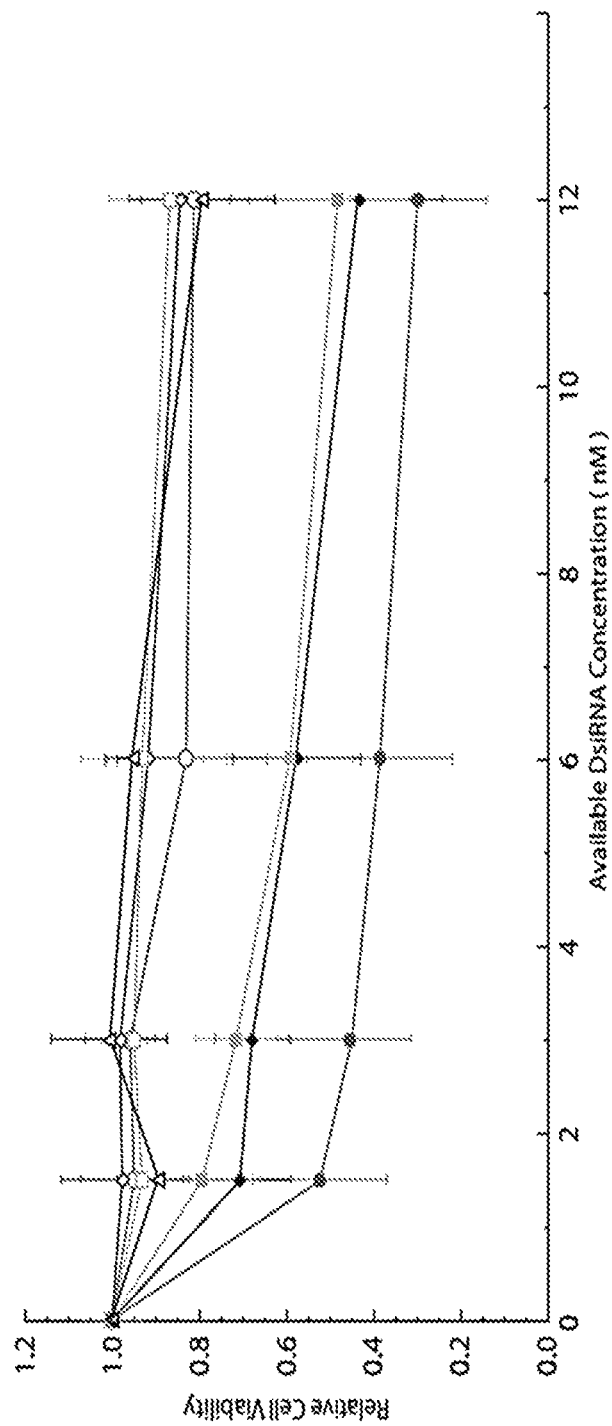

FIG. 6 is a graph showing the results of the use of PLK-1 targeting tetrahedral nanoparticles in therapeutic potency as assessed by cell viability (Y-axis). The X-axis is the available DsiRNA concentration in nM. RNA nanorings (filled diamond), nanocubes (filled squares), and tetrahedral nanoparticles (filled circles) were assembled with DsiRNA arms targeting polo like kinase 1 (PLK-1). The therapeutic potential of the nanoparticles was determined three days after transfection. The eGFP targeting nanorings (open diamonds), the eGFP targeting nanocubes (open squares), the eGFP targeting tetrahedral nanoparticles (open circles), and free eGFP targeting DsiRNA (open triangles) were used as negative controls to determine the extend to which the nanoparticles themselves are cytotoxic. Error bars indicate SD.

Figure 7:
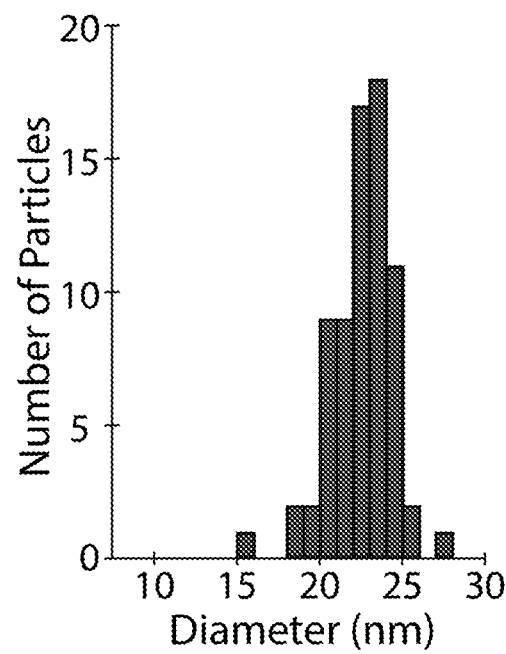

FIG. 7 is a bar graph showing the average diameter (nm) of the inventive tetrahedral nanoparticles as determined by atomic force microscopy.

Figure 8:
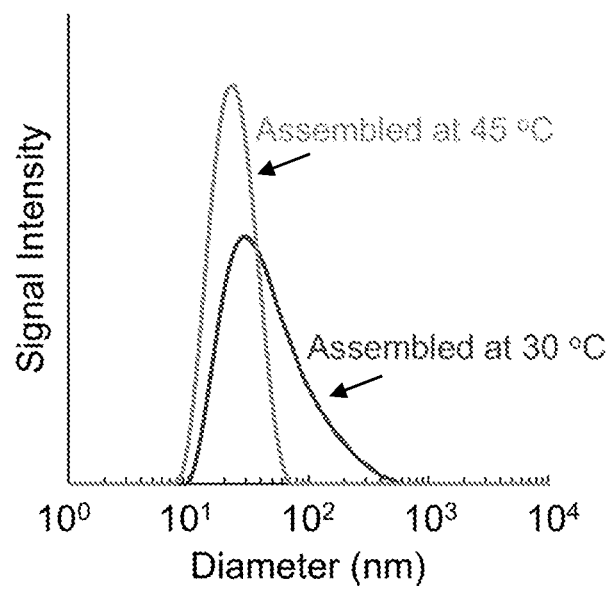

FIG. 8 is a line graph showing the hydrodynamic diameter of the inventive tetrahedral nanoparticles assemble at both 30° C. and 45° C. as determined by dynamic light scattering.

Figure 9:
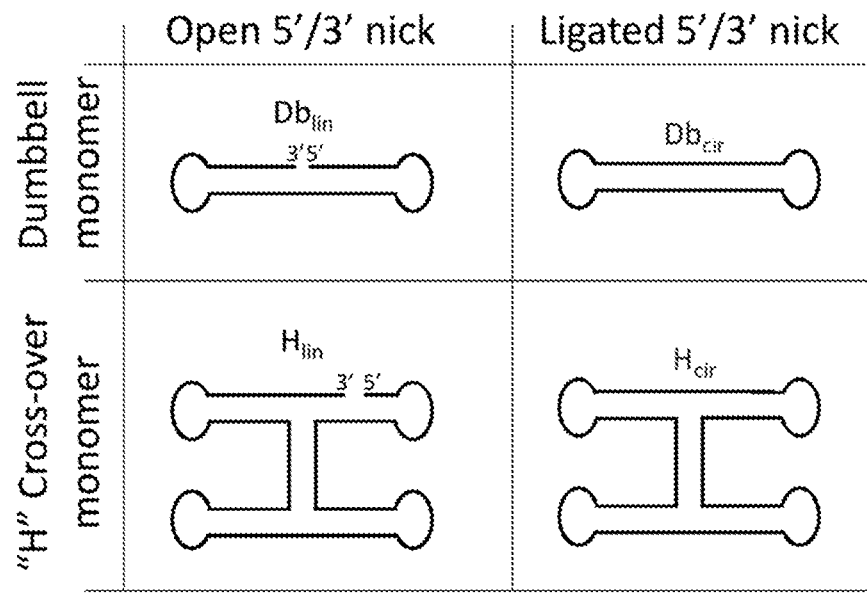

FIG. 9 shows dumbbell monomers (top row) and "H" cross-over monomers (bottom row) with ligated 5'/3' nicks (right column) which creates circularized scaffold monomers.

Figure 10:
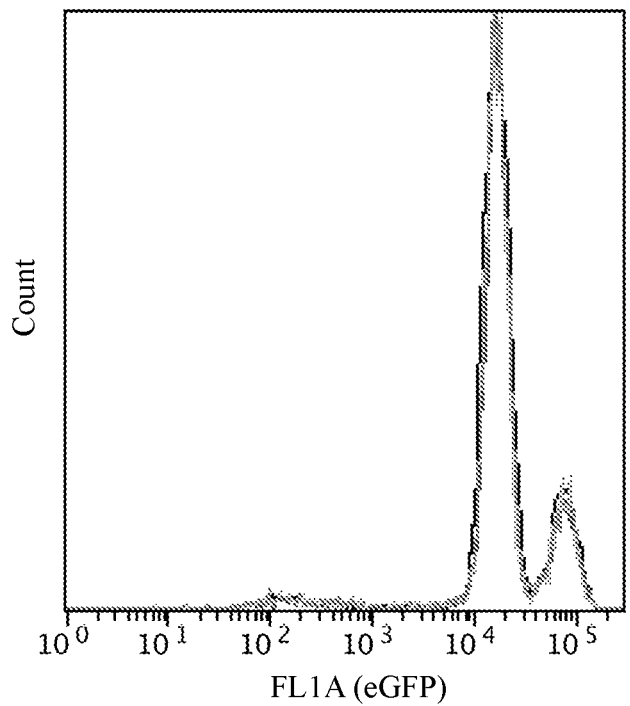

FIG. 10 is a histogram showing the results of a negative control transfection experiment. "Naked" RNA core scaffolds that lacked any DsiRNA arms did not silence the expression of eGFP. The eGFP fluorescence of cells transfected with the non-functionalized nanoring, nanocube or tetrahedral core scaffolds was compared to untreated cells (black) by flow cytometry analysis three days post-transfection. The lines are indistinguishable because none of the nanoparticles silenced expression of the fluorescent protein.

Figure 11:
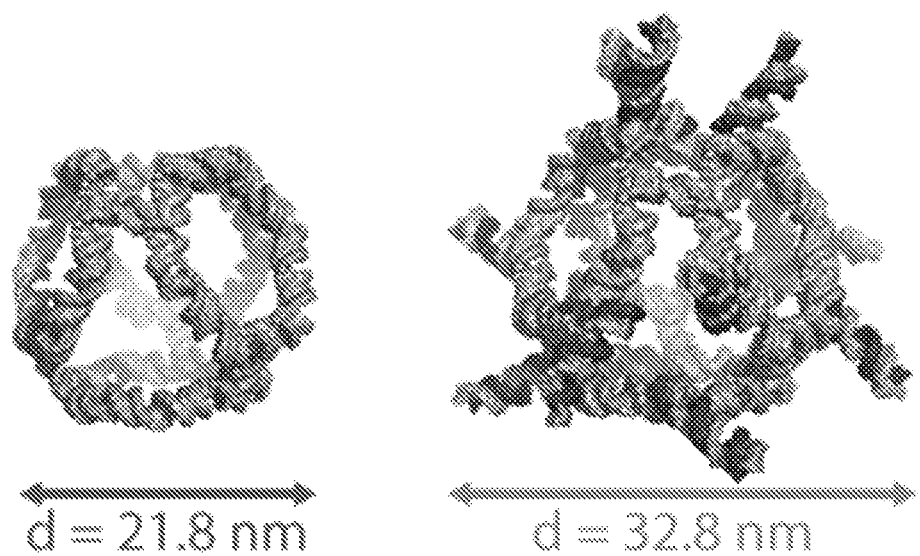

FIG. 11 is an image showing 3D models of the inventive tetrahedral nanoparticles with and without 12 DsiRNA arms.

The radius of gyration was calculated for the 3D model of the inventive tetrahedral nanoparticle without arms at each frame over a 250 ns molecular dynamics trajectory and resulted in an average particle diameter of 21.8 nm+/−0.5. The diameter of the initial minimized 3D model of the inventive tetrahedral nanoparticles with 12 DsiRNA arms was determined to be 32.8 nm.

Figure 12:
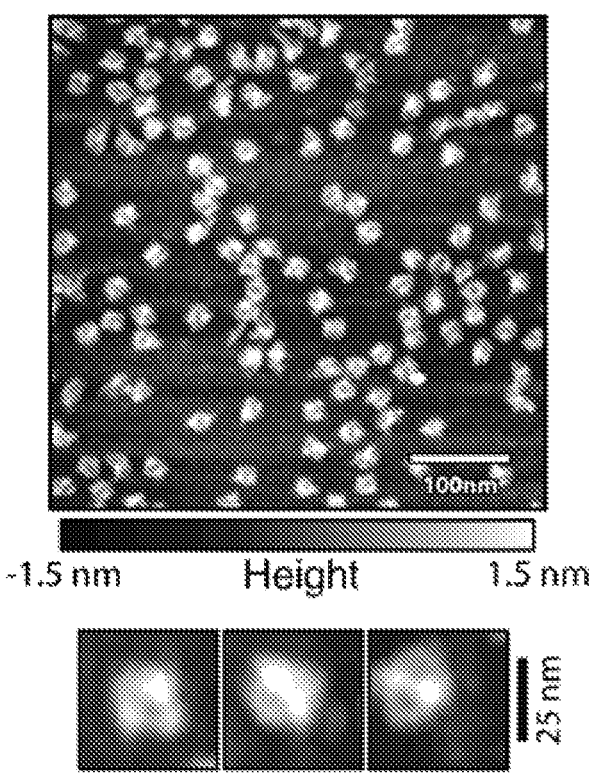

FIG. 12 is another image of the inventive tetrahedral nanoparticles characterized by AFM, imaged in air, according to an embodiment of the invention. The white shapes shown are assembled tetrahedral nanostructures which exhibit relatively uniform size and shape.

Figure 13:
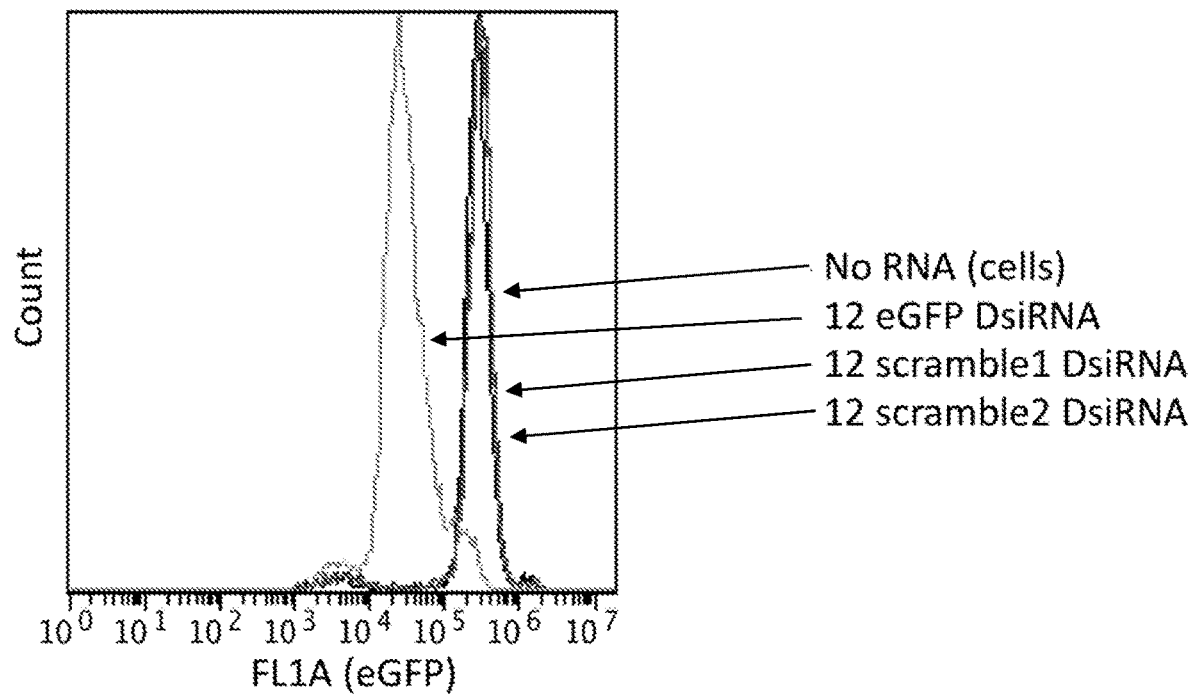

FIG. 13 is a histogram showing the results of another negative control transfection experiment showing that tetrahedral nanoparticles that harbor scrambled DsiRNA sequences do not down regulate eGFP expression. Two different scrambled DsiRNA sequences were incorporated into respective tetrahedral nanoparticles and transfected into cells. eGFP fluorescence was measured three days post transfection by flow cytometry and compared to untreated cells and cells transfected with eGFP targeting tetrahedral nanoparticles.

Figure 14:
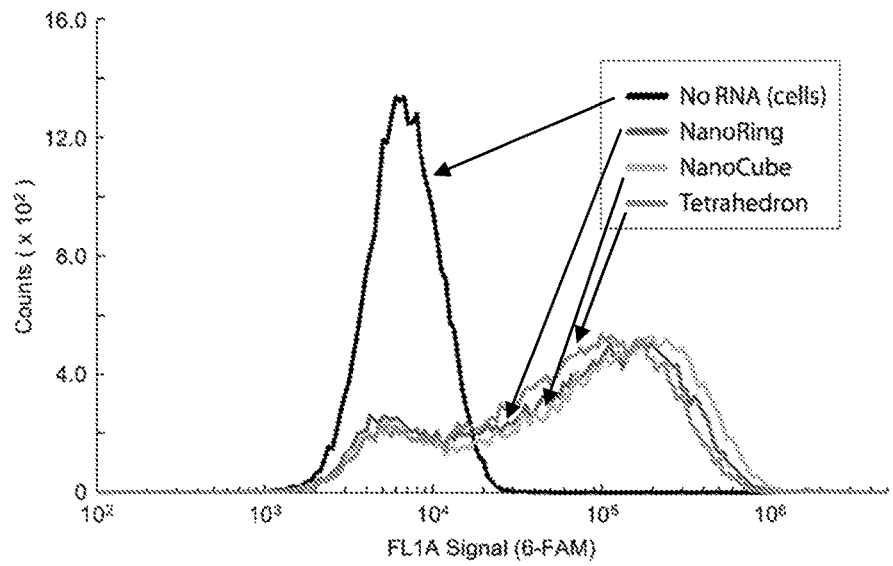

FIG. 14 is a histogram showing the cellular uptake of fluorescently labeled nanoparticles. RNA nanoparticles were assembled with their full complement of DsiRNA moieties (6 DsiRNAs for nanoring and nanocube nanoparticles; 12 DsiRNAs for tetrahedral nanoparticles), with four 6-FAM fluorescent labels per assembled nanoparticle. These labeled RNA nanoparticles were transfected into MDA-MB-231 cells at normalized concentrations such that the number of DsiRNAs was equal in each transfection experiment. The extent of the RNA nanoparticles uptake was assessed after four hours by flow cytometry.

Figure 15:
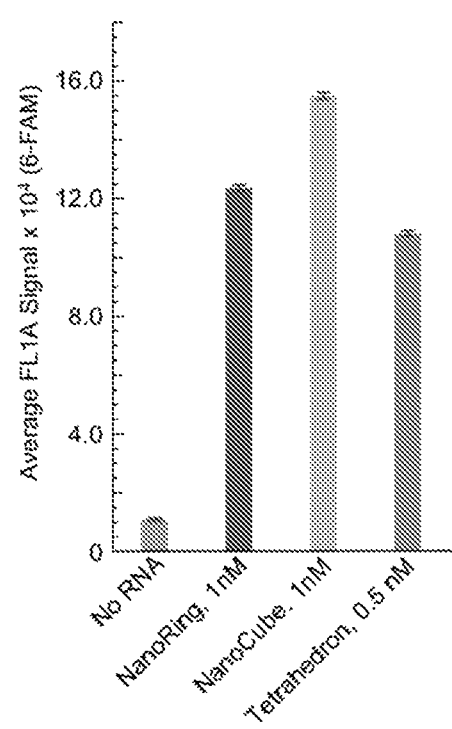

FIG. 15 is a graph showing the average signal of 6-FAM fluorescence of cells treated with RNA nanoparticles following transfection at the indicated NP concentration. Error bars represent SEM.

DETAILED DESCRIPTION OF THE INVENTION

The inventive RNA nanostructures may provide any one or more of a variety of advantages. For example, the hexameric, tetrahedral geometry of the inventive RNA nanostructures may provide a higher order RNA scaffold with one or both of (i) an increased (e.g., double) functional capacity and (ii) enhanced cellular uptake as compared to RNA nanostructures which lack a hexameric, tetrahedral geometry such as, e.g., nanoring and nanocube technologies. The inventive hexameric, tetrahedral RNA nanostructures may comprise up to twelve monomer arms which may be functionalized with any of a variety of functional moieties. RNA nanostructures functionalized with RNA interference substrates may provide enhanced gene silencing efficacy as compared to RNA nanostructures which lack a hexameric, tetrahedral geometry. The inventive RNA nanostructures may, advantageously, maintain a nanoscale size which may facilitate one or both of therapeutic delivery and cellular uptake. Due to the large functional capacity of the inventive nanostructure, any of a variety of avenues for future therapeutic development may be possible. These may include, for example, one or more of (i) targeting of one, two, or more genes with multiple siRNA copies, (ii) targeting up to twelve genes with a single nanostructure (and exploring associated synergistic effects), and (iii) including diagnostic elements (targeting moieties, imaging probes, etc.) while maintaining therapeutic (e.g., DsiRNA) functionality.

An embodiment of the invention provides a nanostructure comprising an RNA scaffold. The scaffold may comprise a hexameric tetrahedral core. The tetrahedral core may comprise four hexameric RNA nanorings linked together. Each hexameric nanoring may comprise dumbbell monomers and cross-over monomers, as described in more detail below.

Each dumbbell monomer may comprise an RNA helix comprising first and second ends. The helix of each dumbbell monomer may be capped at both ends with a kissing loop. A kissing loop is also referred to as an RNA stem-loop, hairpin, or hairpin loop. A kissing loop occurs when two regions of the same RNA strand, usually complementary in nucleotide sequence when read in opposite directions, base-pair to form a double helix that ends in an unpaired loop. RNA kissing complexes (also referred to as kissing interactions) occur when the unpaired nucleotides in one kissing loop base pair with the unpaired nucleotides in another kissing loop. When the kissing loops are located on separate RNA molecules, their intermolecular interaction is called a kissing complex or kissing interaction. Not all stem-loop hairpins are kissing loops. When a stem-loop hairpin does not pair with another stem-loop hairpin, it would not be a kissing loop. Kissing complexes may form from a variety of RNA motifs, including but not limited to RNA I and/or RNA II motifs, RNA I inverse (RNA I) and/or RNA II inverse (RNA II) motifs.

When six dumbbell monomers are present, formation of the kissing complexes results in an approximately 120 degree angle between adjacent helices, which provides the nanoring a hexagonal shape (Yingling et al., *Nano. Lett.*, 7(8): 2328-2334 (2007); Lee et al., *Structure*, 6(8): 993-1005 (1998)). Each hexagonal RNA nanoring contains six kissing complexes. In an embodiment of the invention, the helix of each dumbbell monomer is a helix of about 10 base pair (bp) to about 20 bp. For example, the helix of each dumbbell monomer may be a helix of about 10 bp, about 11 bp, about 12 bp, about 13 bp, about 14 bp, about 15 bp, about 16 bp, about 17 bp, about 18 bp, about 19 bp, or about 20 bp, or a range defined by any two of the foregoing values. Each kissing loop of each dumbbell monomer may be a kissing loop of about 5 nt to about 10 nt. For example, each kissing loop of each dumbbell monomer may be about 5 nt, about 6 nt, about 7 nt, about 8 nt, about 9 nt, about 10 nt, or a range defined by any two of the foregoing values. In a preferred embodiment of the invention, the helix of each dumbbell monomer is a 15 bp helix and each kissing loop of each dumbbell monomer is a 7 nt kissing loop.

The hexameric tetrahedral core may further comprise cross-over monomers. In an embodiment of the invention, each crossover monomer comprises first, second, third, and fourth kissing loops. The cross-over monomer kissing loops may be as described with respect to other aspects of the invention.

As explained above, a kissing complex forms when a kissing loop pairs with another kissing loop with a complementary sequence. In an embodiment of the invention, each of the kissing loops (whether in a dumbbell monomer or a crossover monomer) in a given hexagonal nanoring has a different nucleotide sequence. Accordingly, each one of the heaxagonal nanorings has six kissing complexes, wherein each of the six kissing complexes contains a unique kissing loop sequence paired to a complementary kissing loop sequence in the same nanoring. In this regard, the kissing loop nucleotide sequences advantageously provide a "programmable" system in which the identity and location of each monomer may be predetermined (Grabow et al., *Nano. Lett.*, 11: 878-887 (2011)). The nanorings may self-assemble, wherein the kissing loops anneal to each other, in a sequence-specific manner, in a predicted manner. Each of the unique kissing loop sequences in the nanoring advantageously may have a strong affinity for the respective complementary kissing loop sequence in the nanoring. The unique kissing loop sequences facilitate formation of the hexameric nanoring geometry. Accordingly, in an embodiment of the invention, each kissing loop has a nucleotide sequence that is unique in any one of the nanorings. While the kissing loop nucleotide sequences may be unique within a given nanoring, the same unique kissing loop nucleotide sequence may be common to multiple separate nanorings (e.g., 2, 3, or 4 nanorings) of the hexameric tetrahedral core. Each kissing loop may be, for example, a ColE1-like kissing loop. Examples of kissing loop sequences which may be useful in the inventive nanostructure are underlined in Tables 2A-2E.

Figure 2A:
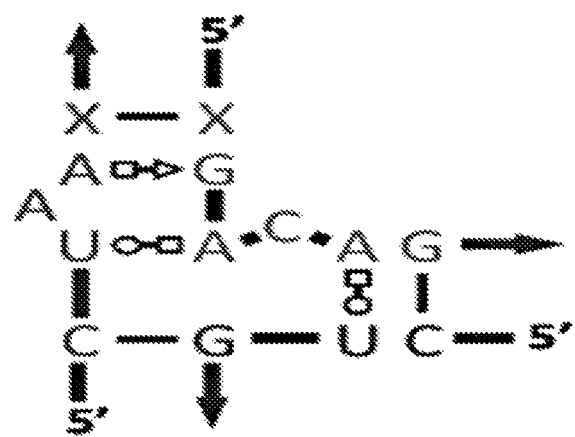

In an embodiment of the invention, each crossover monomer comprises first, second, third, and fourth kissing loops and first and second UA-handle three-way junctions (UAh-3WJs). UAh-3WJs are described, e.g., in Jaeger et al., *Nucleic Acids Res.*, 37(1): 215-230 (2009). A schematic of an example of a UAh-3WJ is shown in FIG. 2A. The UAh-3WJ may be characterized by a central U-A WC:HG trans bp, and may contain 14 tertiary H-bonds and 9 nt stacking interactions. Within its natural ribosomal context, the UAh-3WJs may form arrangements of three helices which are generally T-shaped (e.g., H75-H76-H79 in *Haloarcula marismortui*), where the coaxial stacking of two helices may be enforced and the third stem may protrude at a roughly 90° angle. In an embodiment of the invention, the UAh-3WJs are *Escherichia coli* 23S rRNA UAh-3WJs.

The first and second UAh-3WJs of each crossover monomer may be connected by a bridge helix. The bridge helix connecting the first and second UAh-3WJs may have any length, e.g., about 5 bp, about 6 bp, about 7 bp, about 8 bp, about 9 bp, about 10 bp, about 11 bp, about 12 bp, about 13 bp, about 14 bp, about 15 bp, or a range defined by any two of the foregoing values. In a preferred embodiment, the bridge helix connecting the first and second UAh-3WJs may be a 7 bp helix. The first UAh-3WJ may be positioned symmetrically to the second UAh-3WJ in each crossover monomer. A schematic of an example of a crossover monomer according to an embodiment of the invention is shown in FIG. 2D.

Each crossover monomer may have the general shape of the letter "H." In an embodiment of the invention, the four hexameric RNA nanorings are linked together via "H"-shaped cross-over monomers. Each "H"-shaped cross-over monomer may comprise two UA-handle three-way junctions (3WJs) linked together by a 7 base pair bridge to form the "H"-shaped cross-over monomer.

The first and second UAh-3WJs may be positioned in the crossover monomer in such a way as to provide a tetrahedral geometry. For example, the first UAh-3WJ may be positioned between a first pair of side helices, each of which may, independently, have a length of about 5 bp, about 6 bp, about 7 bp, about 8 bp, about 9 bp, about 10 bp, or a range defined by any two of the foregoing values. In an embodiment of the invention, the lengths of each side helix in the first pair of side helices are not equal to each other. In addition, for example, the second UAh-3WJ may be positioned between a second pair of side helices, each of which may, independently, have a length of about 5 bp, about 6 bp, about 7 bp, about 8 bp, about 9 bp, about 10 bp, or a range defined by any two of the foregoing values. In an embodiment of the invention, the lengths of each side helix in the second pair of side helices are not equal to each other.

In a preferred embodiment of the invention, the first UAh-3WJ may be positioned between a first 8 bp side helix and a first 6 bp side helix. In addition, the second UAh-3WJ may be positioned between a second 8 bp side helix and a second 6 bp side helix. Without being bound to a particular theory or mechanism, it is believed that this positioning of the first and second UAh-3WJs with respect to the 8 bp and 6 bp side helices promotes the tetrahedral geometry of the tetrahedral core.

As described above, each crossover monomer includes four kissing loops. In an embodiment of the invention, a first pair of the four kissing loops of each crossover monomer each may comprise a copy of the same first nucleotide sequence. In addition, a second pair of the four kissing loops of each crossover monomer each may comprise a copy of the same second nucleotide sequence. The second nucleotide sequence may be different from the first nucleotide sequence. Examples of crossover monomer kissing loop sequences which may be useful in the inventive nanostructure are underlined in Table 2E.

The first and second pairs of kissing loops may be positioned in the crossover monomer in such a way as to provide a tetrahedral geometry. In an embodiment of the invention, the first pair of the four kissing loops of each crossover monomer may be positioned symmetrically to one another. Additionally, the second pair of the four kissing loops of each crossover monomer may be positioned symmetrically to one another.

In an embodiment of the invention, each crossover monomer is a single RNA strand. The single RNA strand may have any desired length. For example, the single RNA strand may have a length of about 50 to about 150 nucleotides, about 60 to about 140 nucleotides, about 70 to about 130 nucleotides, about 80 to about 120 nucleotides, or about 90 to about 110 nucleotides. In an embodiment of the invention, the single RNA stand has a length of about 100 nt, about 101 nt, about 102 nt, about 103 nt, about 104 nt, about 105 nt, or a range defined by any two of the foregoing values. In a preferred embodiment, the single RNA strand has a length of 102 nucleotides. In an embodiment of the invention, the single RNA strand is folded to form the crossover monomer.

Figure 2B:
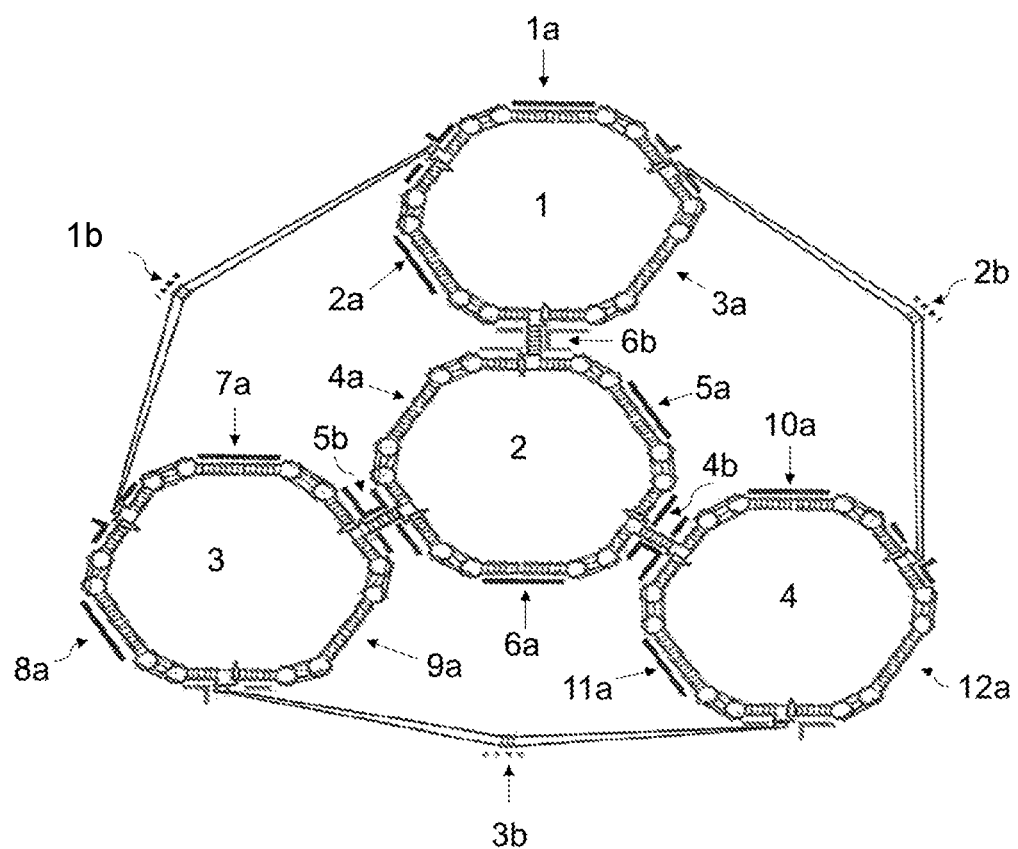

A schematic of an example of a hexameric tetrahedral core according to an embodiment of the invention is shown in FIG. 2B. With reference to FIG. 2B, the tetrahedral core may comprise first (1b), second (2b), third (3b), fourth (4b), fifth (5b), and sixth (6b) cross-over monomers. The tetrahedral core may comprise first (1a), second (2a), third (3a), fourth (4a), fifth (5a), sixth (6a), seventh (7a), eighth (8a), ninth (9a), tenth (10a), eleventh (11a), and twelfth (12a) dumbbell monomers. The first (1a), second (2a), and third (3a) dumbbell monomers and the first (1b), second (2b), and sixth (6b) cross-over monomers together form a first hexameric nanoring (1). The fourth (4a), fifth (5a), and sixth (6a) dumbbell monomers and the fourth (4b), fifth (5b), and sixth (6b) cross-over monomers together form a second hexameric nanoring (2). The seventh (7a), eighth (8a), and ninth (9a) dumbbell monomers and the first (1b), third (3b), and fifth (5b) cross-over monomers together form a third hexameric nanoring (3). The tenth (10a), eleventh (11a), and twelfth (12a) dumbbell monomers and the second (2b), third (3b), and fourth (4b) cross-over monomers together form a fourth hexameric nanoring (4). Each cross-over monomer is shared by two of the hexameric rings to link the hexameric nanorings together to form the hexameric tetrahedral core.

The six crossover monomers and 12 dumbbell monomers assemble to form the hexameric tetrahedral core. In this regard, two of the four kissing loops of each crossover monomer, and one of the two UAh-3WJs of each crossover monomer, are positioned in a first one of the hexameric nanorings. In addition, the other two of the kissing loops of each crossover monomer, and the other one of the UAh-3WJs of each crossover monomer, are positioned in another one of the hexameric nanorings, which is adjacent to, and directly linked to, the first one of the hexameric nanorings.

The hexameric tetrahedral core may comprise two copies of each of three different crossover monomer nucleotide sequences. In this regard, a first pair of the six cross-over monomers may comprise copies of the same first cross-over monomer sequence. A second pair of the six cross-over monomers may comprise copies of the same second cross-over monomer sequence. A third pair of the six cross-over monomers may comprise copies of the same third cross-over monomer sequence. The first, second, and third cross-over monomer sequences may be different from one another. Examples of crossover monomer sequences which may be useful in the inventive nanostructure are provided in Table 2E.

The hexameric tetrahedral core may comprise four copies of each of three different dumbbell monomer nucleotide sequences. In this regard, a first four of the twelve dumbbell monomers may comprise copies of the same first dumbbell monomer sequence. A second four of the twelve dumbbell monomers may comprise copies of the same second dumbbell monomer sequence. A third four of the twelve dumbbell monomers may comprise copies of the same third dumbbell monomer sequence. The first, second, and third dumbbell monomer sequences may be different from one another. Examples of dumbbell monomer sequences which may be useful in the inventive nanostructure are provided in Tables 2A-2D.

The inventive nanostructures may be useful for the delivery of any of a variety of functional moieties. In this regard, the tetrahedral core of the nanostructure may further comprise monomer arms to which a functional moiety may be attached. The monomer arms may be an extension of any of the nucleotide sequences in any of the nanorings of the nanostructure. The tetrahedral core may comprise no monomer arms or any number of monomer arms. In an embodiment of the invention, the tetrahedral core comprises about 1 to about 12 monomer arms. For example, the tetrahedral core may comprise about 1, about 2, about 3, about 4, about 5, about 6, about 7, about 8, about 9, about 10, about 11, about 12, or a range defined by any two of the foregoing values. In a preferred embodiment of the invention, the tetrahedral core comprises four, eight, or twelve monomer arms. Monomer arms for the attachment of functional moieties to RNA nanostructures are described (see, e.g., Afonin et al., *Nano Lett.*, 14: 5662-71 (2014); Grabow et al., *Nano Lett.*, 11: 878-887 (2011)).

In an embodiment of the invention, the monomer arms (e.g., the four, eight, or twelve monomer arms) are each functionalized with one or more functional moieties. The functional moiety may have any desired function such as, for example, a therapeutic, targeting, and/or imaging function. Examples of functional moieties may include, for example, RNA interference (RNAi) substrates, aptamers, small molecules, targeting moieties, imaging probes, proteins (e.g., conjugated proteins), polymers, prodrugs, diagnostic agents, therapeutic agents (e.g., chemotherapeutic agents), pharmaceutical agents, drugs, synthetic organic molecules, peptides, vitamins, and steroids, fluorescent dyes, RNA-DNA hybrids with split functionalities, split lipase, and split GFP. Examples of therapeutic agents (e.g., chemotherapeutic agents) are set forth in WO 2015/171827.

RNA interference (RNAi) substrate may include double-stranded RNA, siRNA, shRNA, or antisense RNA, or a portion thereof, or a mimetic thereof, that when administered to a mammalian cell results in a decrease (e.g., by about 10%, about 25%, about 50%, about 75%, or even about 90 to about 100%) in the expression of a target gene. Typically, an RNAi substrate comprises at least a portion of a target nucleic acid molecule, or an ortholog thereof, or comprises at least a portion of the complementary strand of a target nucleic acid molecule. In an embodiment, the RNAi substrate may comprise a small interfering RNA (siRNA), a short hairpin miRNA (shMIR), a microRNA (miRNA), Dicer substrate RNA (DsiRNA), or an antisense nucleic acid. In an embodiment, the siRNA may comprise, e.g., trans-acting siRNAs (tasiRNAs) and/or repeat-associated siRNAs (rasiRNAs). In another embodiment, the miRNA may comprise, e.g., a short hairpin miRNA (shMIR). In a preferred embodiment, the RNAi substrate comprises DsiRNA. For example, the tetrahedral core may comprise twelve monomer arms, wherein the twelve monomer arms are each functionalized with DsiRNA.

The inventive nanostructure may include a monomer (e.g., a dumbbell monomer or cross-over monomer) with a continuous sequence. In this regard, at least one of (a) the first, second, third, fourth, fifth, and sixth cross-over monomers, and/or at least one of (b) first, second, third, fourth, fifth, sixth, seventh, eighth, ninth, tenth, eleventh, and twelfth dumbbell monomers may comprise a continuous sequence. The continuous sequence is a sequence without 5'/3' breaks. The 5'/3' breaks can be ligated in order to circularize them (i.e., make a sequence with 5'/3' breaks continuous by connecting the 5' end of the sequence to the 3' end of the sequence).

The inventive RNA nanostructures can be formulated into a composition, such as a pharmaceutical composition. In this regard, the invention provides a pharmaceutical composition comprising any of the RNA nanostructures described herein and a pharmaceutically acceptable carrier. The inventive pharmaceutical compositions containing any of the inventive RNA nanostructures can comprise more than one inventive RNA nanostructure, e.g., RNA nanostructures comprising different functional moieties. Alternatively, the pharmaceutical composition can comprise an inventive RNA nanostructures in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for RNA nanostructures. Methods for preparing administrable compositions are known or apparent to those skilled in the art and are described in more detail in, for example, *Remington: The Science and Practice of Pharmacy*, 22nd Ed., Pharmaceutical Press (2012). It is preferred that the pharmaceutically acceptable carrier be one which has no detrimental side effects or toxicity under the conditions of use.

The choice of carrier will be determined in part by the particular inventive RNA nanostructure, the particular functional moiety (or moieties) attached to the RNA nanostructure, as well as by the particular method used to administer the inventive RNA nanostructure. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive RNA nanostructures, and in certain instances, a particular route can provide a more immediate and more effective response than another route. Preferably, the inventive RNA nanostructures are administered by injection, e.g., intravenously.

For purposes of the invention, the amount or dose (e.g., numbers of RNA nanostructures) of the inventive RNA nanostructure administered should be sufficient to effect, e.g., a therapeutic or prophylactic response, in the subject or animal over a reasonable time frame. For example, the dose of the inventive RNA nanostructure should be sufficient to reduce the expression of a target gene or detect, treat or prevent disease (e.g., cancer or a viral disease) in a period of from about 2 hours or longer, e.g., 12 to 24 or more hours, from the time of administration. In certain embodiments, the time period could be even longer. The dose will be determined by the efficacy of the particular inventive RNA nanostructure, the particular functional moiety (or moieties) attached to the nanostructure, and the condition of the animal (e.g., human), as well as the body weight of the animal (e.g., human) to be treated.

Human dosage amounts can initially be determined by extrapolating from the amount of RNA nanostructure used in mice, as a skilled artisan recognizes it is routine in the art to modify the dosage for humans compared to animal models. In certain embodiments it is envisioned that the dosage may vary from between about 1 mg RNA nanostructure/Kg body weight to about 5000 mg RNA nanostructure/Kg body weight; or from about 5 mg/Kg body weight to about 4000 mg/Kg body weight; or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments, this dose may be about 1, about 5, about 10, about 25, about 50, about 75, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600, about 1700, about 1800, about 1900, about 2000, about 2500, about 3000, about 3500, about 4000, about 4500, about 5000 mg/Kg body weight, or a range defined by any two of the foregoing values. In other embodiments, it is envisaged that higher does may be used, such doses may be in the range of about 5 mg RNA nanostructure/ Kg body to about 20 mg RNA nanostructure/Kg body. In other embodiments, the doses may be about 8, about 10, about 12, about 14, about 16 or about 18 mg/Kg body weight. Of course, this dosage amount may be adjusted upward or downward, as is routinely done in such treatment protocols, depending on the results of the initial clinical trials and the needs of a particular patient.

The dose of the inventive RNA nanostructure also will be determined by the existence, nature and extent of any adverse side effects that might accompany the administration of a particular inventive RNA nanostructure. Typically, the attending physician will decide the dosage of the inventive RNA nanostructure with which to treat each individual patient, taking into consideration a variety of factors, such as age, body weight, general health, diet, sex, inventive RNA nanostructure to be administered, route of administration, and the severity of the disease, e.g., cancer being treated.

It is contemplated that the inventive RNA nanostructures may be useful for modulating the expression of a target gene in a mammal. In this regard, an embodiment of the invention provides a method of modulating the expression of a target gene in a mammal, the method comprising administering any of the RNA nanostructures described herein or any of the pharmaceutical compositions described herein in an amount effective to modulate the target gene. In an embodiment of the invention, the expression of the target gene is modulated by increasing the expression of the target gene in the mammal to which the RNA nanostructure is administered as compared to the expression of the target gene in a mammal which has not been administered the RNA nanostructure. In another embodiment of the invention, the expression of the target gene is modulated by decreasing or eliminating the expression of the target gene in the mammal to which the RNA nanostructure is administered as compared to the expression of the target gene in a mammal which has not been administered the RNA nanostructure. The quantity of expression of a target gene may be assayed by methods known in the art.

It is also contemplated that the inventive RNA nanostructures may be useful for treating or preventing a disease in a mammal. In this regard, an embodiment of the invention provides a method of treating or preventing a disease in a mammal, the method comprising administering any of the RNA nanostructures described herein or any of the pharmaceutical compositions described herein in an amount effective to treat or prevent the disease in the mammal.

In an embodiment of the invention, the disease is cancer. The cancer can be any cancer, including any of sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head-neck cancer, acute lymphocytic cancer, acute myeloid leukemia, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer (e.g., colon carcinoma), esophageal cancer, cervical cancer, gastrointestinal carcinoid tumor, hypopharynx cancer, larynx cancer, liver cancer, lung cancer, malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, renal cancer, small intestine cancer, soft tissue cancer, stomach cancer, testicular cancer, thyroid cancer, ureter cancer, and urinary bladder cancer. In an embodiment of the invention, the cancer is breast cancer.

In an embodiment of the invention, the disease is a viral disease. The viral disease may be caused by any virus. In an embodiment of the invention, the viral disease is caused by a virus selected from the group consisting of herpes viruses, pox viruses, hepadnaviruses, papilloma viruses, adenoviruses, coronoviruses, orthomyxoviruses, paramyxoviruses, flaviviruses, and caliciviruses. In an embodiment, the viral disease is caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human T-lymphotropic virus, calicivirus, adenovirus, and Arena virus.

The viral disease may be any viral disease affecting any part of the body. In an embodiment of the invention, the viral disease is selected from the group consisting of influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, and mononucleosis.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a disease in a mammal. Furthermore, the treatment or prevention provided by the inventive method can include treatment or prevention of one or more conditions or symptoms of the viral disease, being treated or prevented. Also, for purposes herein, "prevention" can encompass delaying the onset of the disease, or a symptom or condition thereof.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Another embodiment of the invention provides a method of producing any of the inventive hexameric tetrahedral RNA nanostructures described herein. The method may comprise forming "H"-shaped cross-over monomers. Each "H"-shaped cross-over monomer may comprise two UA-handle three-way junctions (3WJs) linked together by a 7 base pair bridge to form the "H"-shaped cross-over monomer.

The method may further comprise forming hexameric RNA nanorings. Each hexameric RNA nanoring includes three of the "H"-shaped cross-over monomers.

The method may further comprise assembling the hexameric tetrahedral RNA nanostructure. The hexameric tetrahedral RNA nanostructure comprises four of the hexameric RNA nanorings linked together via the "H"-shaped cross-over monomers.

In some embodiments, the method comprises combining nucleic acids (e.g., single-stranded nucleic acids, or oligonucleotides) in a single vessel and allowing the nucleic acids to anneal to each other, based on sequence complementarity. In some embodiments, this annealing process involves placing the nucleic acids at an elevated temperature and then reducing the temperature gradually in order to favor sequence-specific binding. Various nucleic acid nanostructures or self-assembly methods are known.

The following examples further illustrate the invention but, of course, should not be construed as in any way limiting its scope.

EXAMPLES

Three dimensional models were constructed using an RNA architectonics approach. Molecular dynamics (MD) simulations were performed. RNA scaffold strands were transcribed in vitro from PCR amplified DNA. Tetrahedral RNA nanoparticles were assembled in a single-pot reaction. Dynamic light scattering and atomic force microscopy were performed. Cell culture studies, cellular uptake studies, and Plk1 knockdown studies were performed. The following materials and methods were employed in the experiments described in Examples 1 through 8, below.

Three-Dimensional Modeling

Three dimensional models were constructed using an RNA architectonics approach. Previously constructed models of the RNA nanorings were used as the basis for assembling the tetrahedral scaffold model. Initially, four copies of the nanoring were rotated along the x-, y- and z-axes to the proper tetrahedral geometry using the PYMOL molecular visualization program which is available on the internet (PyMOL by Schrödinger). A UA-handle three way junction (Protein Database (PDB) identification: 2AW4; nts 2090-2095, 2194-2201, 2220-2229) was then inserted into appropriate ring monomers, after which a helical segment was inserted to connect the junctions using SWISS PDB-VIEWER (The SIB Swiss Institute of Bioinformatics, available on the website for ExPASy Bioinformatics Resource Portal). To model the tetrahedral scaffold functionalized with Dicer substrate arms, the nanoring faces were replaced with Dicer substrate functionalized ring models that fit previously obtained cryo-electron microscopy (cryo-EM) data. All completed models were rendered using PYMOL (PyMOL by Schrödinger).

Molecular Dynamics Simulations

Molecular dynamics (MD) simulations were performed with the AMBER14 biomolecular simulation package (AMBER molecular simulations website). The RNA-specific force field ff14SB with ff99bsc0 and chi.OL3 parameters was used. The topology and the initial coordinates files were generated with the AMBER LEAP module (AMBER molecular simulations website). Given the size of the tetrahedron model of 1,140 nts and 36,504 atoms, the relatively fast implicit solvent simulations utilizing the Generalized Born model (GB) were employed. Even with the GB approach, the MD simulation proceeded at 1.6 ns/day on an NVIDIA TESLA K40 graphics processing unit (GPU) (NVIDIA, Santa Clara, Calif.). The latest GB-neck2 parameters were used, involving LEAP's intrinsic Born radii parameter mbondi3 and igb=8 Amber MD flag (AMBER molecular simulations website). The implicit solvent dynamics explicit atomic representation of a solute (RNA nanomolecule in this case) is combined with the solvent free energy approximation based on a sum of polar and nonpolar terms. MD simulations employed Langevin thermostat with a collision frequency of $1.0$ $ps^{-1}$ to maintain the 300K temperature and were run with a 2 fs time step and a Debye-Hückel monovalent salt screening concentration of 1.0. No distance cutoff was imposed on nonbonded interactions (cut=999). The SHAKE algorithm was employed to constrain all hydrogen bonds. A six-step equilibration protocol was employed. First the initial model was relaxed with energy minimization. Next, heating to the production run target temperature of 300 K with harmonic restraints of 15 kcal/mol/$Å^2$ applied to the RNA was performed. These initial two steps were followed by short MD stages in which harmonic restraints were gradually lowered from 10.0 (0.25 ns), to 1.0, 0.1, and 0.01 kcal/mol/$Å^2$ (0.5 ns) for the total equilibration time of 2.0 ns. Unrestrained 250 ns-long production MD simulations were performed.

The analyses of the results were performed with scripts utilizing Amber's cpptraj program. The root-mean-square deviation (RMSD) calculations (using cpptraj) were based on the post-equilibration MD trajectory (production runs) with respect to the conformations of the first MD trajectory frame, and all the C4' atoms of the backbone for the full tetrahedron (1,140), and 264 atoms for each hexameric face (i.e. 6×44 backbone atoms, for the pure dumbbells and the face-specific dumbbell parts of the "H"-shaped building blocks linking the four faces). The radius of gyration calculations were performed with the aid of cpptraj (command radgyr) for the entire MD production trajectory, as well as for the energy-minimized model of the tetrahedral scaffold with Dicer substrate arms, including all the atoms of the model.

RNA Synthesis

RNA scaffold strands were transcribed in vitro from PCR amplified DNA. Templates and primers for PCR were purchased from Integrated DNA Technologies, Skokie, Ill. Generally, in vitro transcription reactions were performed using an in-house produced T7 RNA polymerase in 10 mM Tris pH 7.0 buffer containing 5 mM $MgCl_2$, 0.5 mM $MnCl_2$, 2.5 mM NTPs, 2 mM dithiothreitol, 0.01 u/µL inorganic pyrophosphatase, with approximately 50 pmol of DNA template. Transcription products were purified using denaturing polyacrylamide gel electrophoreses (PAGE). Product bands were cut from the gel and eluted overnight at 4° C. in 10 mM Tris pH 7.5 buffer containing 200 mM NaCl and 0.5 mM EDTA, while shaken at 800 rpm. The following day, RNAs were subjected to ethanol precipitation and reconstituted in endotoxin-free water. Short sense and antisense oligonucleotides used to form Dicer substrate RNAs were purchased from Integrated DNA Technologies (Skokie, Ill.) with RNase-free HPLC purification.

Nanoparticle Assembly

Tetrahedral RNA nanoparticles were assembled in a single-pot reaction. Monomeric strands were combined in stoichiometric quantities, heated to 94° C. for 2 minutes (a range of about 90° C. to about 94° C. may be used), followed by snap cooling on ice for 5 minutes to form structured monomer units (Step 1). Assembly buffer was then added to 1× concentration (2 mM $Mg(OAc)_2$, 50 mM KCl, 1×TB buffer [89 mM Tris, 89 mM boric acid, pH 8.2]) and the sample was heated to 45° C. for 30 minutes to carry out the assembly through intermolecular contacts (Step 2). Tetrahedral nanoparticle assembly was assessed by 4.5% acrylamide non-denaturing PAGE (1×TB, 2 mM $Mg(OAc)_2$). RNA nanorings (Table 3A) and nanocubes (Table 3B) were assembled using a single-pot reaction in identical 1× assembly buffer, as previously described in Afonin, et al., *Nat. Protoc.* 6(12): 2022-2034 (2011). For the purpose of cell culture experiments, all RNA nanoparticles were gel purified on 4.5% acrylamide non-denaturing PAGE (1×TB, 2 mM $Mg(OAc)_2$). Product bands were cut from the gel and eluted in 1× assembly buffer overnight, at 4° C. Quantitation of band intensities was performed using IMAGEQUANT5.1 software.

Co-transcriptional assembly of the core tetrahedral scaffold was performed in 10 mM Tris pH 7.0 buffer containing 5 mM $MgCl_2$, 0.5 mM $MnCl_2$, 2.5 mM NTPs, 2 mM dithiothreitol, 0.01 u/µL inorganic pyrophosphatase, and an in-house produced T7 RNA polymerase. The reaction contained six different DNA templates, which included three dumbbell monomers and three H-shaped cross-over monomers (see Table 3C). The amount of each DNA template varied between 2-10 pmol per 10 µL reaction, based on the transcription efficiency of each individual template and the stoichiometry of each monomer in the final assembly. The transcription reaction was allowed to progress for 4 hours at 37° C. After four hours, an aliquot of the transcription mix was loaded onto a 4.5% acrylamide native gel (2 mM $Mg^{2+}$) to check for assembly of the tetrahedral scaffold, along with a control assembly produced by thermal denaturation/renaturation of individually purified monomers.

Dynamic Light Scattering

Samples (75 µL) were prepared at an assembled nanoparticle concentration of 1 µM. Once assembled, samples were centrifuged at 14,000×g for 1 hr and 4° C. to pellet any debris. Following centrifugation, the top 70 µL were transferred to the cuvette for sizing. Sizing experiments were performed using a ZETASIZER NANO ZS (Malvren Instruments, Malvern, UK.). Particles sizes are reported as the average from three separate measurements plus/minus the standard deviation of the measurements.

Atomic Force Microscopy

Atomic Force Microscopy (AFM) substrates were prepared as described in Lyubchenko et al., *Methods*, 54(2): 274-283 (2011). Briefly, 100 µL of 167 µM 1-(3-aminopropyl) silatrane (APS) were deposited onto freshly cleaved V-1 grade mica disks (Ted Pella Inc., Redding, Calif.), covered, and incubated at room temperature for 20 minutes. The disks were then rinsed thoroughly under PICO-PURE water (Hydro, Duram, N.C.), dried under a stream of nitrogen, and placed under vacuum for at least 20 minutes. The substrates were stored in a dry box until use.

RNA constructs were diluted to 10 nM in assembly buffer. Then, 20 µL of the 10 nM solution was deposited on freshly prepared APS mica substrates, and incubated for 3 minutes at room temperature, rinsed in PICO-PURE water (Hydro, Duram, N.C.), and dried with compressed nitrogen immediately prior to imaging.

AFM images of the constructs were collected using a CYPHER-VRS AFM video-rate AFM operating in ambient tapping mode (Asylum Research, Santa Barbara, Calif.) using AC240TS-R3 probes (Olympus, Center Valley, Pa.). Images were processed and analyzed using Asylum's software. Briefly, the raw images were first-order flattened to remove sample tilt, and single constructs were segmented from the image (aggregates and incompletely assembled particles were excluded from the analysis). For each segmented particle, characteristic lengths, areas, heights, and properties derived from those values were measured and calculated by the software's particle analysis module. The reported diameter is the diameter of a circle with a perimeter equal to that of the segmented particle. The measured planar dimensions of the constructs are larger than the true values due to tip broadening. The probe tip has a nominal radius of 7 nm.

Cell Culture Studies

The MDA-MB-231 cells used for this study were cultured in high glucose DULBECCO MODIFIED EAGLE MEDIUM (Millipore Sigma, Kankakee, Ill.) supplemented with 10% fetal bovine serum, 100 u/mL penicillin and 100 µg/mL streptomycin and grown in a humidified incubator at 37° C. with 5% $CO_2$. Unless otherwise stated, transfection reactions were prepared as follows. For eGFP silencing studies, MDA-MB-231 cells that stably express eGFP were seeded in 24 well plates at 30,000 cells per well, 24 hours prior to transfection. Aliquots of 2 µL LIPOFECTAMINE 2000 transfection reagent (Thermo Fisher, Waltham, Mass.) in 20 µL OPTI-MEM reduced serum media (Thermo Fisher) were prepared to which the RNA samples were added and allowed to complex for 20 minutes at room temperature. OPTI-MEM reduced serum media (Thermo Fisher) was added to a final volume of 500 µL, growth media was aspirated from wells, and RNA/L2K/OPTIMEM transfection samples were added to the cells. Transfections were carried out for 4 hours at 37° C., after which the transfection media was removed and replaced with complete growth media. Three days post transfection, cells were washed with 1×PBS, lifted from the plate, and eGFP fluorescence was assessed using a BD ACCURI C6 flow cytometer (BD Biosciences US, San Jose, Calif.).

Cellular Uptake Studies

Cellular uptake studies were performed using non-eGFP expressing MDA-MB-231 cells. Cells were seeded at 50,000 cells per well in 24 well plates, 24 hours prior to transfection. Transfection experiments were prepared as described above. Four hours post-transfection, the transfection media was removed, cells were lifted, and the extent of cellular uptake was assessed by measuring the 6-FAM fluorescence of cells using a BD ACCURI C6 flow cytometer (BD Biosciences US).

Plk1 Knockdown Studies

Plk1 knockdown studies were performed using non-eGFP expressing MDA-MB-231 cells. Cells were seeded in 96 well plates at 7,500 cells/well, 24 hours prior to transfection. Aliquots of 1.5 µL LIPOFECTAMINE 2000 transfection reagent (Thermo Fisher) in 15 µL OPTI-MEM reduced serum media (Thermo Fisher) were prepared to which RNA samples were added and allowed to complex for 20 minutes at room temperature. OPTI-MEM reduced serum media (Thermo Fisher) was added to a final volume of 300 µL, growth media was aspirated from wells, and RNA/L2K/OPTIMEM transfection samples were added to the cell. Transfections were carried out for 4 hours at 37° C., after which the transfection media was removed and replaced with complete growth media. Three days post transfection cell viability was assessed by staining cells using VIA-STAIN Hoechst/PI Viability Kit (Nexcelom Bioscience, Lawrence, Mass.) and imaged using a CELIGO IMAGE cytometer (Nexcelom Bioscience, Lawrence, Mass.). Staining and imaging were performed in accordance with the manufacturer's instructions. Relative cell viability for a sample was calculated as the fraction of live cells with respect to samples that received mock (OPTI-MEM reduced serum media only) transfections.

Example 1

This example demonstrates the design and computational modeling of the inventive tetrahedral nanoparticles.

Figure 1A:
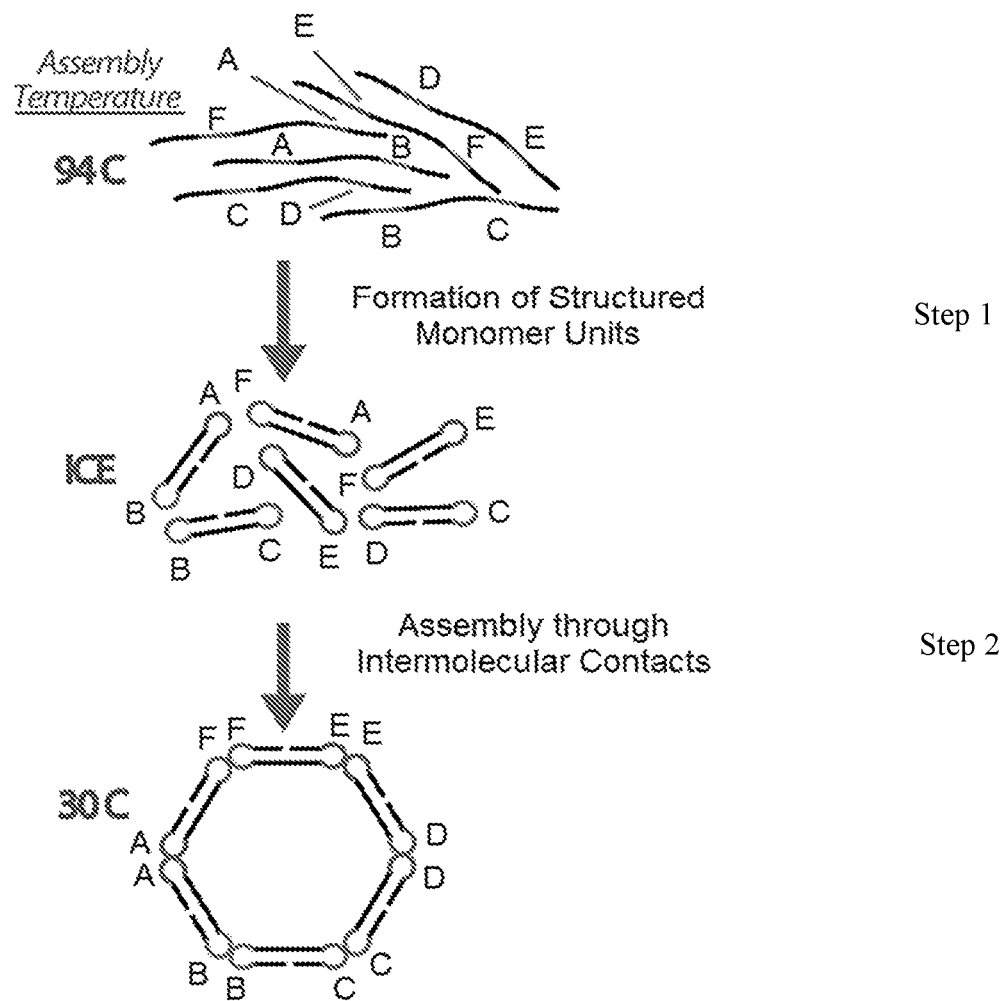
Figure 1B:
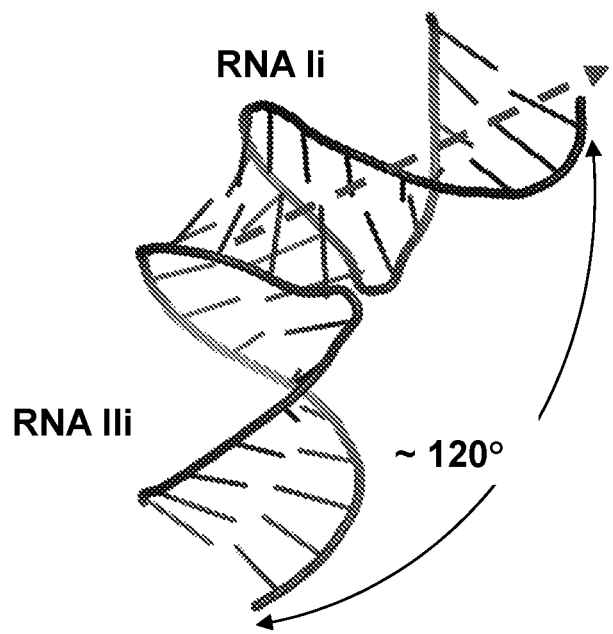

The tetrahedral scaffold was designed using an RNA architectonics approach, where naturally occurring structural motifs are used to define specific geometries and contacts for intermolecular assembly. The monomeric units of the tetrahedral scaffold, as well as the method of monomer self-assembly, were based on the design and structure of the previously characterized RNA nanoring, as described in Grabow, et al., *Nano Lett.*, 11(2): 878-887 (2011), and Yingling, et al., *Nano Lett.*, 7(8): 2328-2334 (2007). The RNA nanoring was comprised of six dumbbell-shaped monomer units that assemble through the formation of inverted ColE1-like kissing complexes, as shown in FIGS. 1A and 1B. Each dumbbell monomer contained a central 15 base pair (bp) helix, capped at both ends with a 7 nucleotide (nt) ColE1-like kissing loop. Formation of the kissing complex resulted in an approximate 120 degree angle between adjacent helices (FIG. 1B), giving the RNA nanoring a hexagonal shape when six monomers are present. Each of the six kissing complexes that defined the nanoring differed in their primary nucleotide sequence, resulting in a fully-programmable system where the identity and location of each monomer unit was predetermined.

The newly developed tetrahedral scaffold was structured from four modified RNA nanorings (FIG. 2B). Each of the four nanorings involved an individual face of the complete inventive tetrahedral structure. While each nanoring face was assembled through non-covalent kissing complex formation, each face was covalently tethered to one another through the incorporation of a newly designed monomer unit. The new "H"-shaped cross-over monomer folded as a single strand of RNA and replaced the two dumbbell monomers which were adjacent in 3D space, but assembled as part of two separate nanoring faces. Each cross-over monomer contains two UA-handle three-way junctions (UAh-3WJ) derived from the *Escherichia coli* 23S rRNA (FIG. 2A). UAh-3WJ was chosen because it was hypothesized that this 3WJ can form structurally rigid monomers within the context of a supramolecular RNA nanostructure. One UAh-3WJ was integrated into each of the adjacent dumbbells that was ultimately replaced the new cross-over monomer (Table 3C). Emanating from these 3WJs, a 7 bp helix was inserted that spaned the gap between the two adjacent dumbbells. The result was a single 102 nt RNA strand that replaced two 44 nt dumbbell monomers. Each cross-over monomer unit contained four kissing loops, which allowed it to be incorporated into the assembly of two neighboring nanorings, and thus covalently linked neighboring faces in the assembled tetrahedral structure (FIG. 2B). As the nanorings exhibit a hexagonal geometry, the negative space between the nanorings was triangular, giving the assembled structure a truncated tetrahedral geometry. In total, the assembled tetrahedral scaffold contained twelve dumbbell monomers and six "H"-shaped cross-over monomers (FIG. 2B; Table 3C).

Figure 2C:
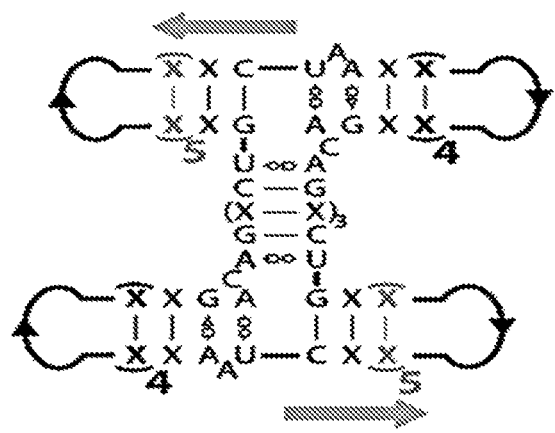
Figure 2D:
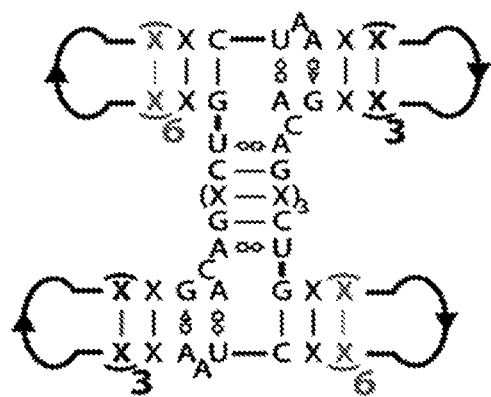
Figure 2E:
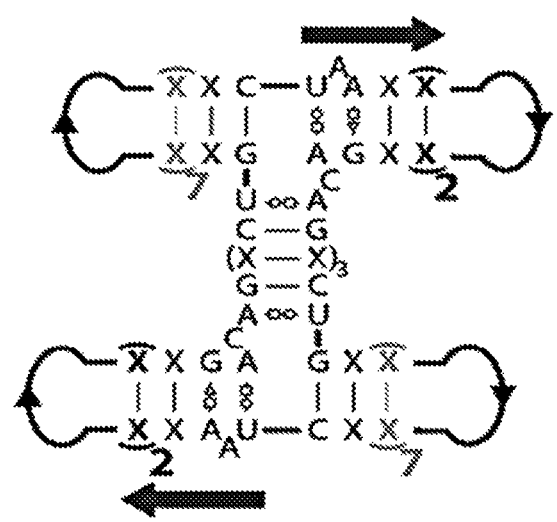

A three-dimensional model of the tetrahedral scaffold was manually constructed using SWISS PDB-VIEWER (The SIB Swiss Institute of Bioinformatics, available on the website for ExPASy Bioinformatics Resource Portal) and existing RNA structural data available in the PDB. To construct the cross-over monomers that were required to connect neighboring nanoring faces, the UAh-3WJ was inserted and modeled in various positions along adjacent dumbbell monomers. The 3WJs were slid down the dumbbell monomers at 1 base pair (bp) increments to determine the optimal orientation of the 3WJ in order to angle the connected rings in a tetrahedral geometry (FIGS. 2C, 2D, and 2E). The advantageous position of the 3WJ to promote tetrahedral geometry of the nanoring faces was found to have helices of 8 bp and 6 bp on either side of the junction (FIG. 2D). The two 3WJs were positioned within the dumbbell elements symmetrically, such that the cross-over monomer could be rotated 180° and maintain an identical structure. The four kissing loop sequences incorporated within the each cross-over monomer was arranged symmetrically, such that both of the dumbbell elements encoded the same two loop sequences. This ensured that each unique cross-over monomer occupied the same position within each nanoring face and afforded the greatest degree of programmable control over construct assembly with the fewest number of unique kissing complex sequences. The symmetry of the 3WJs and kissing loop sequences also allowed for the cross-over monomers to assemble in either possible orientation (0° or rotated 180°) without altering the position of the short junction-spanning helix relative to the larger assembly. Modeling of the 3' Dicer substrate arms of the functionalized tetrahedral nanoparticle was based on the orientation of the Dicer substrate arms emanating from hexameric nanorings described in Afonin et al., *Nano Lett* 14(10): 5662-5671 (2014). The completed initial model(s) were used to project a secondary structure diagram from which the primary nucleotide sequence was designed. Defined sequence constraints included the UAh-3WJ motif, as well as the six ColE1-like kissing complexes. Sequences for helical regions were then designed to promote proper secondary structure folding of the individual monomer units.

Example 2

This example demonstrates that molecular dynamics simulations suggest a structurally robust scaffold for the inventive tetrahedral nanoparticles.

Implicit solvent molecular dynamics (MD) was used to study the structural integrity of the tetrahedral scaffold. Initial minimization was performed on the constructed model, followed by a 250 ns MD run. Over the course of the MD run the tetrahedral scaffold remained intact and resistant to large structural perturbations, maintaining an average root mean squared deviation (RMSD) of 10.9 Å. Some structural deformation was observed within individual monomer units and resulted in distortion of the nanoring faces away from an ideal hexametric geometry. However, these distortions were not significant enough to disrupt the kissing complexes that facilitate nanoparticle assembly. Overlays of structural snapshots taken every 25 ns of the MD run highlighted that while there is definitive motion of individual monomers, the tetrahedral geometry persists throughout. Even the maximal RMSD structure (16.2 Å) obtained 136.74 ns into the run, exhibited a structure that highly resembled the initial minimized model, suggesting that this tetrahedral supramolecular structure is likely to exhibit significant thermodynamic stability. The minimal RMSD structure (7.70 Å) was obtained about 95 ns into the run.

Due to the use of 3WJ containing cross-over monomers, in which a single RNA strand is incorporated into the assembly of two nanorings, the distribution of 5'/3' strand breaks among the four nanoring faces is not equal, as shown in FIGS. 3A-3D. As mentioned above, the symmetric design of the cross-over monomers means that each could assemble in two possible orientation (0° or rotated 180°), meaning its 5'/3' strand break could be present in either one of the two nanoring assemblies in which the monomer is incorporated. Because each nanoring face requires three dumbbell monomers to assemble, the number of 5'/3' strand breaks attributed these dumbbell monomers is equal in each face. However, as the assembled tetrahedron utilizes six cross-over monomers to link together four nanorings, three different distributions of 5'/3' breaks attributed to the cross-over monomers are possible (5'/3' breaks attributed to dumbbell monomers are equal in each face; each contains three dumbbell breaks) (FIGS. 3A-3D). One possible distribution of cross-over monomer 5'/3' breaks is a tetrahedral assembly where each nanoring face has a different number of 5'/3' breaks: 3 breaks in the first face, 2 breaks in the second face, 1 break in the third face, and no breaks in the fourth (3,2,1,0 distribution, FIG. 3A). However, it is also possible for the assembly to contain three faces with 2 strand breaks and the fourth face is without any cross-over monomer strand breaks (2,2,2,0 distribution, FIG. 3B), or a scenario where two faces each have two strand breaks, and two faces each have one (2,2,1,1 distribution, FIG. 3C).

Figure 3A:
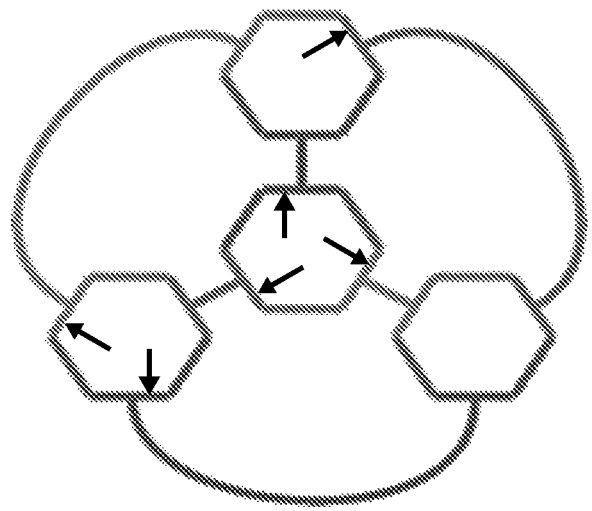
FIG. 3A is a schematic showing the 3, 2, 1, 0 distribution of the 5'/3' breaks possible within the cross-over monomer, according to an embodiment of the invention.
Figure 3B:
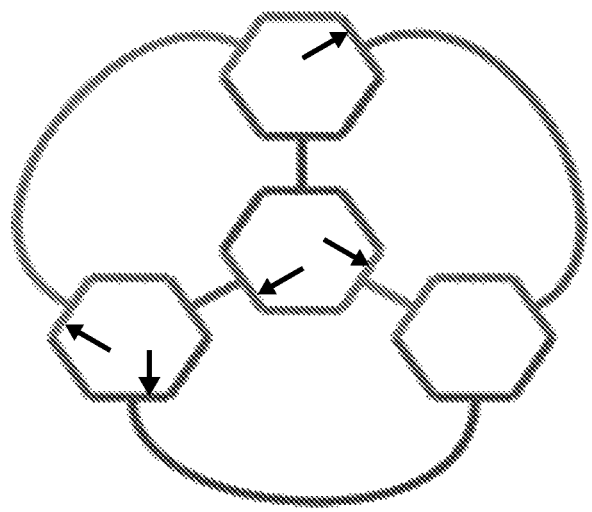
FIG. 3B is a schematic showing the 2, 2, 2, 0 distribution of the 5'/3' breaks possible within the cross-over monomer, according to an embodiment of the invention.
Figure 3C:
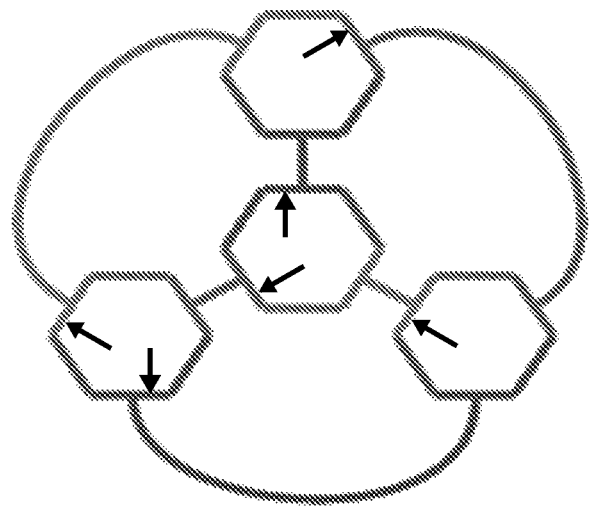
FIG. 3C is a schematic showing the 2, 2, 1, 1 distribution of the 5'/3' breaks possible within the cross-over monomer, according to an embodiment of the invention.
Figure 3D:
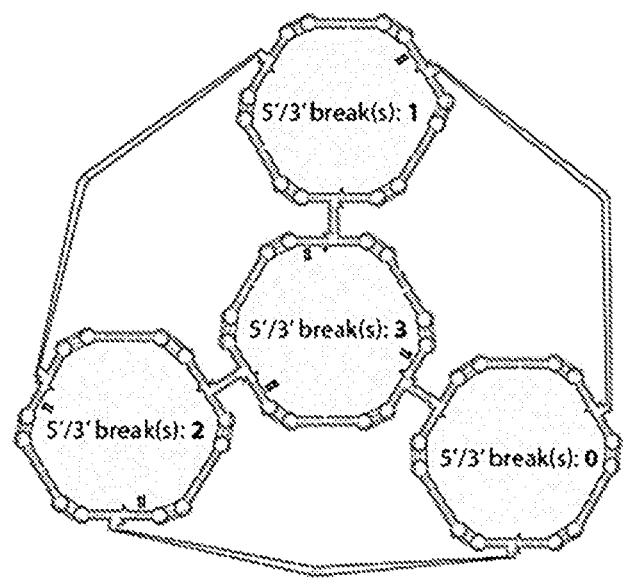
FIG. 3D is a schematic of a 3-D model subjected to molecular dynamics simulation which indicates the 5'/3' breaks attributed to the H-monomers, as shown in the secondary structure, according to an embodiment of the invention.

In addition to monitoring the total RMSD for the entire tetrahedral scaffold, the RMSD of each individual nanoring face was also examined over the course of the MD run (Table 1). The 3D model used for the MD simulations contained a 3, 2, 1, 0 distribution of cross-over monomer associated 5'/3' strand breaks (FIG. 3A). However, the number of cross-over monomer 5'/3' breaks within a nanoring face displayed no correlation to the degree of structural distortion over the course of MD, as measured by RMSD. This suggests it is unlikely for there to exist a thermodynamic bias towards a particular distribution of 5'/3' strand breaks with the assembly, and that the distribution of the 5'/3' strand breaks is unlikely to significantly affect the stability of the tetrahedral assembly. The cross-over monomer structure, overall particle structure, and the relative positioning of programmable monomer units are not affected by changes in the position of cross-over associated 5'/3' strand breaks.

TABLE 1

| Tetrahedral Face | Number of 5'/3' breaks of H-monomers | Average RMSD in Å found over the course of the MD simulation |
| --- | --- | --- |
| A | 0 | 7.63 ± 0.96 |
| B | 1 | 7.28 ± 1.22 |
| C | 2 | 7.47 ± 1.14 |
| D | 3 | 8.18 ± 1.18 |

Example 3

This example demonstrates the assembly and characterization of the inventive tetrahedral scaffold.

The core tetrahedral scaffold is assembled from six unique RNA sequences (Table 3C), using a 2:1 stoichiometry of dumbbell monomers to cross-over monomers (Table 3C). Because only six unique sequences are used to assemble the tetrahedral core, each of the four nanoring faces are identical in terms of monomer and kissing loop composition. The tetrahedral scaffold can be assembled in a one-pot reaction that closely mirrors the protocol used to the assembled individual nanorings. Monomer strands were mixed in their stoichiometric quantities and thermally denatured, snap cooled on ice to promote intramolecular secondary structure formation, followed by incubation at 45° C. to allow for supramolecular assembly of the scaffold. Scaffold assembly assessed by non-denaturing PAGE indicated that this one-pot protocol yielded a single assembly product. Temperatures higher or lower than 45° C. for the incubation step appeared to be detrimental for scaffold assembly. Interestingly, material that is observed to be stuck in the wells during electrophoresis does not appear to be misfolded or large oligomeric structures. Instead, it appeared that they are properly assembled structures that aggregate at the gel/buffer interface and prevent additional material from entering the gel, presumably due to the large size of the tetrahedral nanostructure.

The tetrahedral scaffold can also be assembled using a co-transcriptional assembly approach, where the six DNA templates encoding the six monomer sequences are simultaneously transcribed in a single reaction vesicle in which they assemble into the defined nanostructure. While the tetrahedral scaffold assembles isothermally at 37° C. during transcription, the assembly yield appeared to be slightly improved by raising the temperature 45° C. following transcription. In the case of co-transcriptional assembly, the concentration of individual templates in the reaction mix are not stoichiometric to ratios of transcribed monomer units in the final assembly, as each DNA template is transcribed with different efficiency. Optimization of template concentrations and buffer conditions are required to enhance the yield of complete, properly assembled scaffolds.

Verification and characterization of the assembled tetrahedral scaffold was performed using several techniques. The initial characterization by non-denaturing PAGE showed that assembly of the core scaffold produced a single defined product. This was verified by dynamic light scattering (DLS) measurements, where a single sizing peak accounted for approximately 90% of the measured signal. These DLS measurements indicated that the core tetrahedral scaffold had a hydrodynamic diameter of approximately 25 nm, making the scaffold slightly bigger than the predicted 21.8 nm+/−0.5 diameter, calculated as the average radius of gyration of the 3D model over the course of the molecular dynamics simulation (Table 4). Visualization of the core scaffold was performed using AFM and further verified the formation of discrete, nanoscale objects exhibiting relatively uniform size and shape (FIGS. 4A-4D and 12).

Additional sizing analysis of 72 non-overlapping nanostructures imaged by AFM concluded that the adsorbed tetrahedral scaffolds are oblong with average lengths of 24.6+/−3.4 nm and widths of 22.5+/−3.2 nm, corresponding to a circle with an average equivalent diameter of 22.5 nm+/−1.8 (FIGS. 7, 11, and 12), in good agreement with both the predicted scaffold size based on 3D modeling and the hydrodynamic diameter as measured by DLS.

Experiments also indicate that the tetrahedral scaffold is more thermodynamically stable than a simpler bi-nanoring structure assembled using a single cross-over monomer to link together two nanorings. The nanoring "dimer" is more susceptible to thermal melting than the more complex, three-dimensional tetrahedral structure assembled from four ring-structures.

Taken together, characterization of the core scaffold suggests robust assembly of discrete, stable tetrahedral nanostructures.

Example 4

This example demonstrates the functionalization of the inventive tetrahedral scaffold with Dicer substrate siRNAs.

Tetrahedral nanoparticles can be functionalized by replacing the 44 nt dumbbell monomer strands with sequences that contain additional sequence elements added to the 5' or 3' end of the dumbbell (Table 3C). Replacing one, two, or all three dumbbell monomers with sequences that contain siRNA antisense extensions at their 3' ends produces tetrahedral nanoparticles with four, eight or twelve Dicer substrate siRNAs (DsiRNAs), respectively, when a corresponding sense-coding strand is present in the assembly mix. The resulting 12 DsiRNA-adorned tetrahedral nanoparticles were also subjected to DLS characterization, identical to that performed on the naked core scaffold. The fully DsiRNA-functionalized particles exhibit a hydrodynamic diameter of 32.8 nm±0.5 as determined by DLS, in agreement with the diameter predicted from the 3D model of the functionalized nanoparticle. As was the case with the core scaffold, the DsiRNA functionalized tetrahedral nanoparticle appears to form a single, discrete specie upon assembly, as indicated by both non-denaturing PAGE and the single peak observed during DLS experiments.

Example 5

This example demonstrates that the inventive tetrahedral nanoparticles invoke enhanced RNAi-mediated gene silencing.

The potential of the tetrahedral nanostructure to be used as a scaffold for RNAi-based therapeutic delivery was first assessed by transfection into cultured MDA-MB-231 human breast cancer cells that stably express enhanced green fluorescent protein (eGFP). Tetrahedral nanoparticles harboring DsiRNAs targeting eGFP were compared to the previously developed RNA nanoring and RNA nanocube delivery scaffolds, in addition to free DsiRNAs (FIG. 5A). Transfection of MDA-MB-231 cells with equimolar concentrations of assembled particles revealed that the tetetrahedral NP is superior to nanorings, nanocubes, and free DsiRNA duplexes in terms of eGFP silencing (FIG. 5A, left). However, when the concentration of delivered material is normalized to the assembled particle, the tetrahedral NP effectively delivers twice the number of DsiRNA duplexes compared to rings and cube (12 versus 6), and twelve times more than free DsiRNAs alone. To account for this discrepancy in available DsiRNA concentration, additional transfection experiments were performed with normalized concentrations of DsiRNAs. For every one tetrahedral nanoparticle, double the amount of nanoring or nanocube nanoparticles were used, evening out the number of DsiRNA duplexes present in the transfection mix. Even after doubling the concentration of nanorings and nanocubes, the tetrahedral nanoparticles displayed a greater degree of eGFP silencing than the other constructs tested (FIG. 5A, right). Notably, all three nanoparticles display greater silencing of eGFP expression than an equimolar concentration of free DsiRNAs, as assessed by flow cytometry.

Two possible scenarios could explain the increased RNAi efficacy observed for tetrahedral nanoparticles: (1) increasing the number of Dicer substrate siRNAs delivered on a single nanoparticle could enhance its silencing efficacy, or (2) some physical characteristic of the scaffold (size, shape, relative positioning of DsiRNAs, etc.) influences the efficiency by which its adorned DsiRNAs ultimately enter into the RNAi pathway. The possibility that the number of DsiRNAs harbored by a single nanoparticle influences its down-stream RNAi efficacy was addressed by assembling tetrahedral, nanoring and nanocube nanoparticles such that each nanoparticle was functionalized with only four Dicer substrate siRNAs.

Tables 2A-2J, below, provide the RNA sequences used in this study, indicated by names and SEQ ID NO.

Table 2A provides the nanoring dumbbell scaffold monomers (5' to 3'). In Table 2A, the kissing loop sequences are underlined.

TABLE 2A

| SEQ ID NO. | Name | Sequence |
|---|---|---|
| 1 | NR-A | GGGAAUCCGUCCACUGGAUUCCCGUCACAGAGCCUGCCUGUGAC |
| 2 | NR-B | GGGAAUCCGCAGGCUGGAUUCCCGUCACAGAGAACGCCUGUGAC |
| 3 | NR-C | GGGAAUCCGCGUUCUGGAUUCCCGUCACAGACGUCUCCUGUGAC |
| 4 | NR-D | GGGAAUCCGAGACGUGGAUUCCCGUCACAGUCGUGGUCUGUGAC |
| 5 | NR-E | GGGAAUCCACCACGAGGAUUCCCGUCACAGAACCAUCCUGUGAC |
| 6 | NR-F | GGGAAUCCGAUGGUUGGAUUCCCGUCACAGAGUGGACCUGUGAC |

Table 2B provides the nanoring dumbbell monomers functionalized with enhanced green fluorescent protein (eGFP) DsiRNA antisense (5' to 3'). In Table 2B, the kissing loop sequences are underlined; eGFP antisense sequence are in bold.

TABLE 2B

| SEQ ID NO. | Name | Sequence |
|---|---|---|
| 7 | NR-A.gfp | GGGAACC<u>GUCCACU</u>GGUUCCCGCUACGAGA<u>GCCUG</u>CCUCGUAGCUUCGGUGGUGCAGAUGAACUUCAGGGUCA |
| 8 | NR-B.gfp: | GGGAACC<u>GCAGGC</u>UGGUUCCCGCUACGAGA<u>GAACG</u>CCUCGUAGCUUCGGUGGUGCAGAUGAACUUCAGGGUCA |
| 9 | NR-C.gfp: | GGGAACC<u>GCGUUC</u>UGGUUCCCGCUACGAGA<u>CGUCU</u>CCUCGUAGCUUCGGUGGUGCAGAUGAACUUCAGGGUCA |
| 10 | NR-D.gfp: | GGGAACC<u>GAGACG</u>UGGUUCCCGCUACGAGU<u>CGUGG</u>UCUCGUAGCUUCGGUGGUGCAGAUGAACUUCAGGGUCA |
| 11 | NR-E.gfp: | GGGAACC<u>ACCACG</u>AGGUUCCCGCUACGAGA<u>ACCAU</u>CCUCGUAGCUUCGGUGGUGCAGAUGAACUUCAGGGUCA |
| 12 | NR-F.gfp: | GGGAACC<u>GAUGGU</u>UGGUUCCCGCUACGAGA<u>GUGGA</u>CCUCGUAGCUUCGGUGGUGCAGAUGAACUUCAGGGUCA |

Table 2C provides nanoring dumbbell monomers functionalized with negative control (ncl) DsiRNA antisense (5' to 3'). In Table 2C, the kissing loop sequences are underlined; ncl antisense sequence are in bold.

TABLE 2C

| SEQ ID NO. | Name | Sequence |
|---|---|---|
| 13 | NR-B.ncl | GGGAACC<u>GCAGGC</u>UGGUUCCCGCUACGAGA<u>GAACGC</u>UCGUAGCUUAUACGCGUAUUAUACGCGAUUAACGAC |
| 14 | NR-D.ncl | GGGAACC<u>GAGACG</u>UGGUUCCCGCUACGAGU<u>CGUGGU</u>CUCGUAGCUUAUACGCGUAUUAUACGCGAUUAACGAC |
| 15 | NR-E.ncl | GGGAACC<u>ACCACG</u>AGGUUCCCGCUACGAGA<u>ACCAUC</u>CUCGUAGCUUAUACGCGUAUUAUACGCGAUUAACGAC |
| 16 | NR-F.ncl | GGGAACC<u>GAUGGU</u>UGGUUCCCGCUACGAGA<u>GUGGAC</u>CUCGUAGCUUAUACGCGUAUUAUACGCGAUUAACGAC |

Table 2D provides nanoring dumbbell monomers functionalized with polo like kinase 1 (plk1) DsiRNA antisense (5' to 3'). In Table 2D, the kissing loop sequences are underlined; plk1 antisense sequence are in bold.

TABLE 2D

| SEQ ID NO. | Name | Sequence |
|---|---|---|
| 17 | NR-A.plk1 | GGGAACC<u>GUCCACU</u>GGUUCCCGCUACGAGA<u>GCCUGCC</u>UCGUAGCUUUCGUCAUUAAGCAGCUCGUUAAUGGUU |
| 18 | NR-B.plk1 | GGGAACC<u>GCAGGC</u>UGGUUCCCGCUACGAGA<u>GAACGCC</u>UCGUAGCUUUCGUCAUUAAGCAGCUCGUUAAUGGUU |
| 19 | NR-C.plk1 | GGGAACC<u>GCGUUC</u>UGGUUCCCGCUACGAGA<u>CGUCUCC</u>UCGUAGCUUUCGUCAUUAAGCAGCUCGUUAAUGGUU |
| 20 | NR-D.plk1 | GGGAACC<u>GAGACG</u>UGGUUCCCGCUACGAGU<u>CGUGGUC</u>UCGUAGCUUUCGUCAUUAAGCAGCUCGUUAAUGGUU |
| 21 | NR-E.plk1 | GGGAACC<u>ACCACG</u>AGGUUCCCGCUACGAGA<u>ACCAUCC</u>UCGUAGCUUUCGUCAUUAAGCAGCUCGUUAAUGGUU |
| 22 | NR-F.plk1 | GGGAACC<u>GAUGGU</u>UGGUUCCCGCUACGAGA<u>GUGGACC</u>UCGUAGCUUUCGUCAUUAAGCAGCUCGUUAAUGGUU |

Table 2E provides tetrahedral nanoparticle "cross-over" monomers (5' to 3'). In Table 2E, kissing loop sequences are underlined; junction sequences are in italics.

TABLE 2E

| SEQ ID NO. | Name | Sequence |
|---|---|---|
| 23 | TET-A | GGUG<u>UCCACU</u>ACCCUCGACAGAAUC*UG*ACAUC<u>AGCCUGC</u>GAUGU*CUA*AGACAUG<u>GUCCACU</u>CAUGUCGA*CA*GAUUC*UG*CACAG<u>AGCCUGC</u>CUGUGC*UA*AGAG |
| 24 | TET-C | GGUG<u>CGUUC</u>UACCCUCGACAGAAUC*UG*ACAUC<u>ACGUCUC</u>GAUGU*CUA*AGACAUG<u>GCGUUC</u>U CAUGUCGA*CA*GAUUC*UG*CACAG<u>ACGUCUC</u>CUGUGC*UA*AGAG |
| 25 | TET-E | GGG<u>ACCACGA</u>CCCGCUGACAGAAUC*UG*ACAUC<u>AACCAUC</u>GAUGU*CUA*AGACAUG<u>ACCACGA</u>CAUGUCGA*CA*GAUUC*UG*CACAG<u>AACCAUC</u>CUGUGC*UA*AAGC |

Table 2F provides nanocube scaffold monomers (5' to 3').

TABLE 2F

| SEQ ID NO. | Name | Sequence |
|---|---|---|
| 26 | Cb-A | GGCAACUUUGAUCCCUCGGUUUAGCGCCGGCCUUUUCUCCCACACUUUCACG |
| 27 | Cb-B | GGGAAAUUUCGUGGUAGGUUUUGUUGCCCGUGUUUCUACGAUUACUUUGGUC |
| 28 | Cb-C | GGACAUUUUCGAGACAGCAUUUUUUCCCGACCUUUGCGGAUUGUAUUUAGG |
| 29 | Cb-D | GGCGCUUUUGACCUUCUGCUUUAUGUCCCCUAUUUCUUAAUGACUUUUGGCC |
| 30 | Cb-E | GGGAGAUUUAGUCAUUAAGUUUUACAAUCCGCUUUGUAAUCGUAGUUUGUGU |
| 31 | Cb-F | GGGAUCUUUACCUACCACGUUUUGCUGUCUCGUUUGCAGAAGGUCUUUCCGA |

Table 2G provides nanocube monomers functionalized with enhanced green fluorescent protein (eGFP) DsiRNA antisense (5' to 3'). eGFP antisense sequences are in bold.

TABLE 2G

| SEQ ID NO. | Name | Sequence |
|---|---|---|
| 32 | Cb-A.gfp | GGCAACUUUGAUCCCUCGGUUUAGCGCCGGCCUUU UCUCCCACACUUUCACGUUCGGUGGUGCAGAUGAA CUUCAGGGUCA |
| 33 | Cb-B.gfp | GGGAAAUUUCGUGGUAGGUUUUGUUGCCCGUGUUU CUACGAUUACUUUGGUCUUCGGUGGUGCAGAUGAA CUUCAGGGUCA |
| 34 | Cb-C.gfp | GGACAUUUUCGAGACAGCAUUUUUUCCCGACCUUU GCGGAUUGUAUUUUAGGUUCGGUGGUGCAGAUGAA CUUCAGGGUCA |
| 35 | Cb-D.gfp | GGCGCUUUUGACCUUCUGCUUUAUGUCCCCUAUUU CUUAAUGACUUUUGGCCUUCGGUGGUGCAGAUGAA CUUCAGGGUCA |
| 36 | Cb-E.gfp | GGGAGAUUUAGUCAUUAAGUUUUACAAUCCGCUUU GUAAUCGUAGUUUGUGUUUCGGUGGUGCAGAUGAA CUUCAGGGUCA |
| 37 | Cb-F.gfp | GGGAUCUUUACCUACCACGUUUUGCUGUCUCGUUU GCAGAAGGUCUUUCCGAUUCGGUGGUGCAGAUGAA CUUCAGGGUCA |

Table 2H provides nanocube monomers functionalized with negative control (ncl) DsiRNA antisense (5' to 3'). In Table 2 H, ncl antisense sequence is in bold.

TABLE 2H

| SEQ ID NO. | Name | Sequence |
|---|---|---|
| 38 | Cb-E.ncl | GGGAGAUUUAGUCAUUAAGUUUUACAAUCCGCUUU GUAAUCGUAGUUUGUGUUUAUACGCGUAUUAUACG CGAUUAACGAC |
| 39 | Cb-F.ncl | GGGAUCUUUACCUACCACGUUUUGCUGUCUCGUUU GCAGAAGGUCUUUCCGAUUAUACGCGUAUUAUACG CGAUUAACGAC |

Table 2I provides nanocube monomers functionalized with polo like kinase 1 (plk1) DsiRNA antisense (5' to 3'). In Table 2I, plk1 antisense sequence is in bold.

TABLE 2I

| SEQ ID NO. | Name | Sequence |
|---|---|---|
| 40 | Cb-A.plk1 | GGCAACUUUGAUCCCUCGGUUUAGCGCCGGCCUUU UCUCCCACACUUUCACGUUUCGUCAUUAAGCAGCU CGUUAAUGGUU |
| 41 | Cb-B.plk1 | GGGAAAUUUCGUGGUAGGUUUUGUUGCCCGUGUUU CUACGAUUACUUUGGUCUUUCGUCAUUAAGCAGCU CGUUAAUGGUU |
| 42 | Cb-C.plk1 | GGACAUUUUCGAGACAGCAUUUUUUCCCGACCUUU GCGGAUUGUAUUUUAGGUUUCGUCAUUAAGCAGCU CGUUAAUGGUU |

TABLE 2I-continued

| SEQ ID NO. | Name | Sequence |
|---|---|---|
| 43 | Cb-D.plk1 | GGCGCUUUUGACCUUCUGCUUUAUGUCCCCUAUUU CUUAAUGACUUUUGGCCUUUCGUCAUUAAGCAGCU CGUUAAUGGUU |
| 44 | Cb-E.plk1 | GGGAGAUUUAGUCAUUAAGUUUUACAAUCCGCUUU GUAAUCGUAGUUUGUGUUUUCGUCAUUAAGCAGCU CGUUAAUGGUU |
| 45 | Cb-F.plk1 | GGGAUCUUUACCUACCACGUUUUGCUGUCUCGUUU GCAGAAGGUCUUUCCGAUUCGGUGGUGCAGAUGAA CUUCAGGGUCA |

Table 2J provides corresponding DsiRNA sense and fluorescently labeled strands (5' to 3'). In Table 2J, (p) denotes a 5' monophosphate; dN denotes deoxynucleotide.

TABLE 2J

| SEQ ID NO: | Name and sequence |
|---|---|
| 46 | eGFP DsiRNA sense:<br>(p) ACCCUGAAGUUCAUCUGCACCACCG |
| 47 | (6-FAM) eGFP DNA sense; DNA sense strand labeled with 6-carboxyfluorescein (6-FAM):<br>(6-FAM) dAdCdCdCdTdGdAdAdGdTdTdCdAdTdCdTdGd CdAdCdCdAdCdCdG |
| 48 | ncl DsiRNA sense:<br>(p) CGUUAAUCGCGUAUAAUACGCGUAU |
| 49 | plk1 DsiRNA sense:<br>(p) CCAUUAACGAGCUGCUUAAUGACGA |

Tables 3A, 3B, and 3C, below, provide the monomers used to assemble various RNA nanostructures described herein. The copy number per assembled nanoparticle is indicated for each strand. The SEQ ID NOs for each of the monomers referred to in Tables 3A-3C are provided in Tables 2A-2J.

Table 3A provides nanoring structures.

TABLE 3A

| Core Scaffold | 6 eGFP DsiRNA | 4 eGFP DsiRNA | 6 plk1 DsiRNA | (6-FAM) labeled | Ring Dimer |
|---|---|---|---|---|---|
| NR-A (× 1) | NR-A.gfp (× 1) | NR-A (× 1) | NR-A.plk1 (× 1) | NR-A.gfp (× 1) | NR-A (× 2) |
| NR-B (× 1) | NR-B.gfp (× 1) | NR-B.gfp (× 1) | NR-B.plk1 (× 1) | NR-B.nc1 (× 1) | NR-B (× 2) |
| NR-C (× 1) | NR-C.gfp (× 1) | NR-C.gfp (× 1) | NR-C.plk1 (× 1) | NR-C.gfp (× 1) | NR-C (× 2) |
| NR-D (× 1) | NR-D.gfp (× 1) | NR-D (× 1) | NR-D.plk1 (× 1) | NR-D.gfp (× 1) | NR-D (× 2) |
| NR-E (× 1) | NR-E.gfp (× 1) | NR-E.gfp (× 1) | NR-E.plk1 (× 1) | NR-E.nc1 (× 1) | TET-E (× 1) |
| NR-F (× 1) | NR-F.gfp (× 1) | NR-F.gfp (× 1) | NR-F.plk1 (× 1) | NR-F.gfp (× 1) | NR-F (× 2) |
|  | eGFP sense (× 6) | eGFP sense (× 4) | plk1 sense (× 6) | nc1 sense (× 2) |  |
|  |  |  |  | (6-FAM) eGFP |  |
|  |  |  |  | DNA sense (× 4) |  |

Table 3B provides nanocube structures.

TABLE 3B

| Core Scaffold | 6 eGFP DsiRNA | 4 eGFP DsiRNA | 6 plk1 DsiRNA | (6-FAM) labeled |
|---|---|---|---|---|
| Cb-A (× 1) | Cb-A.gfp (× 1) | Cb-A.gfp (× 1) | Cb-A.plk1 (× 1) | Cb-A.gfp (× 1) |
| Cb-B (× 1) | Cb-B.gfp (× 1) | Cb-B.gfp (× 1) | Cb-B.plk1 (× 1) | Cb-B.gfp (× 1) |
| Cb-C (× 1) | Cb-C.gfp (× 1) | Cb-C.gfp (× 1) | Cb-C.plk1 (× 1) | Cb-C.gfp (× 1) |
| Cb-D (× 1) | Cb-D.gfp (× 1) | Cb-D.gfp (× 1) | Cb-D.plk1 (× 1) | Cb-D.gfp (× 1) |
| Cb-E (× 1) | Cb-E.gfp (× 1) | Cb-E (× 1) | Cb-E.plk1 (× 1) | Cb-E.nc1 (× 1) |
| Cb-F (× 1) | Cb-F.gfp (× 1) | Cb-F (× 1) | Cb-F.plk1 (× 1) | Cb-F.nc1 (× 1) |
|  | eGFP sense (× 6) | eGFP sense (× 4) | plk1 sense (× 6) | nc1 sense (× 2) |
|  |  |  |  | (6-FAM) eGFP |
|  |  |  |  | DNA sense (× 4) |

Table 3C provides tetrahedral structures.

TABLE 3C

| Core Scaffold | 12 eGFP DsiRNA | 4 eGFP DsiRNA | 12 plk1 DsiRNA | (6-FAM) labeled |
|---|---|---|---|---|
| TET-A (× 2) | TET-A (× 2) | TET-A (× 2) | TET-A (× 2) | TET-A (× 2) |
| NR-B (× 4) | NR-B.gfp (× 4) | NR-B.gfp (× 4) | NR-B.plk1 (× 4) | NR-B.gfp (× 4) |
| TET-C (× 2) | TET-C (× 2) | TET-C (× 2) | TET-C (× 2) | TET-C (× 2) |
| NR-D (× 4) | NR-D.gfp (× 4) | NR-D (× 4) | NR-D.plk1 (× 4) | NR-D.nc1 (× 4) |
| TET-E (× 2) | TET-E (× 2) | TET-E (× 2) | TET-E (× 2) | TET-E (× 2) |
| NR-F (× 4) | NR-F.gfp (× 4) | NR-F (× 4) | NR-F.plk1 (× 4) | NR-F.nc1 (× 4) |
|  | eGFP sense (× 12) | eGFP sense (× 4) | plk1 sense (× 12) | nc1 sense (× 8) |
|  |  |  |  | (6-FAM) eGFP |
|  |  |  |  | DNA sense (× 4) |

Table 4, below, provides the size estimates of the tetrahedral scaffold and functionalized tetrahedral nanoparticles based on the radius of gyration measurements of corresponding three-dimensional models.

TABLE 4

| Modeled Structure | Condition | Diameter (nm) |
|---|---|---|
| Tetrahedral Scaffold | Initial minimized model | 20.0 |
|  | Last MD frame at 250 ns | 21.6 |
|  | Average of all MD time steps | 21.8 ± 0.5 |
| 12DsiRNA Functionalized Tetrahedral Nanoparticle | Minimized model | 32.8 |

Following transfection with equimolar concentrations of nanoparticles (and therefore equal DsiRNA, the tetrahedral NP again displayed superior knockdown of eGFP compared to nanorings and nanocubes harboring an equal number of DsiRNA arms (FIG. 5B). This suggests that some physical characteristic of the tetrahedral nanoparticle is contributing to its increased silencing efficacy.

Additional control gene silencing experiments were performed to measure the eGFP fluorescence. The nanoparticles without any DsiRNA extensions were transfected into MDA-MB-231 breast cancer cells stably expressing eGFP. Specifically, the tetrahedral nanoparticles, nanocubes, nanorings, and control (no RNA) were used. As seen in FIG. 10, the nanoparticles did not silence expression of the fluorescent protein meaning that the previously observed silencing is attributable to the activity of the DsiRNA arms. Additionally, it was found that scrambled DsiRNA sequences (see Tables 5A and 5B) did not silence expression of the fluorescent protein meaning that the previously observed silencing is attributable to the sequences of the DsiRNA arms (FIG. 13).

TABLE 5A

| SEQ ID NO. | Name | Sequence |
|---|---|---|
| 50 | NR-B.scrmb1 | GGGAAUCC*GCAGGCUG*GAUUCCCGUCACAGAGAAC*GCCUGUGACUU*GAUGCGCGUAGUCCGUAUGGCUAAGAG |
| 51 | NR-D.scrmb1 | GGGAAUCC*GAGACGUG*GAUUCCCGUCACAG*UCGUGGUCUGUGACUU*GAUGCGCGUAGUCCGUAUGGCUAAGAG |
| 52 | NR-F.scrmb1 | GGGAAUCC*GAUGGUUG*GAUUCCCGUCACAGA*GUGGACCUGUGACUU*GAUGCGCGUAGUCCGUAUGGCUAAGAG |

TABLE 5B

| SEQ ID NO. | Name | Sequence |
|---|---|---|
| 53 | NR-B.scrmb2 | GGGAAUCC*GCAGGCUG*GAUUCCCGUCACAGAGA*ACGCCUGUGACUU*GCUUCCGGGUGCAAUGGAAGGUGAUAC |
| 54 | NR-D.scrmb2 | GGGAAUCC*GAGACGUG*GAUUCCCGUCACAG*UCGUGGUCUGUGACUU*GCUUCCGGGUGCAAUGGAAGGUGAUAC |
| 55 | NR-F.scrmb2 | GGGAAUCC*GAUGGUUG*GAUUCCCGUCACAGA*GUGGACCUGUGACUU*GCUUCCGGGUGCAAUGGAAGGUGAUAC |

In Tables 5A and 5B, the kissing loop sequences are underlined and the scramble antisense sequences are in italics.

Cellular uptake experiments were then performed using MDA-MB-231 cells that did not express eGFP. The nanoring, nanocube and tetrahedral nanoparticles that were used for uptake studies each contained their full complement of DsiRNA appendages (6, 6, and 12 respectively). However, only four DsiRNAs of each nanoparticle were labeled with a fluorescent tag, normalizing the fluorescent intensity per nanoparticle. A combination of monomer units coding two different DsiRNA antisense extensions were used in order to label only a subset of the DsiRNA arms on each nanoparticle. eGFP antisense extensions were paired with DNA sense coding strands tagged with a fluorescent label at its 5' end, while the remaining DsiRNAs encoded a non-targeting negative control sequence (ncl). Surprisingly, the tetrahedral nanoparticles displayed a far greater degree of cellular uptake than either the nanoring or nanocube nanoparticles at equal nanoparticle concentrations and when the concentration used for uptake is normalized based on the number of DsiRNA, more nanorings and nanocubes are taken up than tetrahedron nanoparticles (in these conditions, twice as many nanorings and nanocubes are in the transfection mix, because they have ½ the number of DsiRNAs) as compared to the tetrahedron nanoparticles (FIGS. 5C, 5D, 14 and 15).

This evidence suggests that the size and/or shape of the tetrahedral nanoparticle plays a significant role in gaining entry into the cell, and thus ultimately affects the effectiveness of the RNAi therapeutic. Surprisingly, regardless of the level of cellular uptake of the nanoparticles, the inventive tetrahedral nanoparticles showed increased silencing meaning they are more effective than nanoparticles of other shapes.

Example 6

This example demonstrates that the targeting of polo-like kinase 1 with the inventive tetrahedral nanoparticles results in substantial loss of cell viability.

Ultimately, the goal of using RNAi-based therapeutics is to be able to alter cellular function and/or survival through the down regulation of a target gene(s). While it appears clear that the use of tetrahedral RNA nanoparticles invoke a superior RNAi response as compared to other RNA nanoparticles examined, as evident by the relative knockdown of eGFP fluorescence, it is unclear within this system if the increased degree of gene silencing would translate into increased alteration of cellular function. To assess the modulation of endpoint cellular function through RNAi-mediated gene silencing, RNA nanoparticles were designed with Dicer substrate elements that targeted polo-like kinase 1 (PLK1) mRNA (FIG. 6).

PLK1 plays a role in regulating the cell cycle at the level of spindle formation and chromosome separation, and is overexpressed in many forms of cancer. Depletion of PLK1 is known to result in growth inhibition and induction of apoptosis. In the current study, MDA-MB-231 cells that do not express eGFP were transfected with PLK1-targeting nanoparticles with each NP bearing its maximum number of DsiRNA arms. The concentration of each nanoparticle delivered was normalized so that the concentration of DsiRNA present in the transfection media was equal between RNA nanoparticles with differing numbers of DsiRNA arms. Cells were assessed for viability three days post-transfection. Of the three plk1-targeting RNA nanoparticles examined, the tetrahedral nanoparticles were the most potent, showing the greatest reduction in cell viability across each concentration assayed (FIG. 6). Negative control transfections of nanoparticles harboring eGFP targeting DsiRNAs revealed that the tetrahedral RNA nanoparticles are no more cytotoxic than either of the other nanoparticles examined, or free DsiRNAs, despite the tetrahedral NP's significantly larger mass.

Example 7

This example further characterizes the inventive tetrahedral nanoparticles.

DLS was used to assess and confirm the assembly temperatures of the inventive tetrahedral nanoparticles, and components thereof.

As seen in FIG. 8, the inventive tetrahedral nanoparticles assemble at 45° C. and 30° C., however, assembly of the inventive tetrahedral nanoparticles at 45° C. is preferred because assembly of the inventive tetrahedral nanoparticles at 30° C. resulted in the formation of larger, less homogenous particles, as determined by dynamic light scattering.

Example 8

This example demonstrates that circularization of the scaffold monomers within the inventive tetrahedral nanoparticles provides added thermodynamic stability and increased resistance to exonuclease degradation.

As seen in FIG. 9, the dumbbell monomers and "H" cross-over monomers (bottom row) were circularized by ligating the 5'/3' nicks. The circularization of the scaffold monomers was completed using an established protocol. The circularization of the scaffold increased thermodynamic stability and resistance to exonuclease degradation.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A tetrahedral nanostructure comprising a ribonucleic acid (RNA) scaffold comprising a core, wherein the core comprises four hexameric RNA nanorings linked together, and wherein the nanostructure has a truncated tetrahedral geometry.

2. The nanostructure according to claim 1, wherein the four hexameric RNA nanorings linked are together via "H"-shaped cross-over monomers,
wherein each "H"-shaped cross-over monomer comprises two UA-handle three-way junctions (3WJs) linked together by a 7 base pair bridge to form the "H"-shaped cross-over monomer.

3. A nanostructure comprising a ribonucleic acid (RNA) scaffold comprising a hexameric tetrahedral core, wherein the tetrahedral core comprises:
first, second, third, fourth, fifth, and sixth cross-over monomers;
first, second, third, fourth, fifth, sixth, seventh, eighth, ninth, tenth, eleventh, and twelfth dumbbell monomers;
wherein the first, second, and third dumbbell monomers and the first, second, and sixth cross-over monomers together form a first hexameric nanoring;
wherein the fourth, fifth, and sixth dumbbell monomers and the fourth, fifth, and sixth cross-over monomers together form a second hexameric nanoring;
wherein the seventh, eighth, and ninth dumbbell monomers and the first, third, and fifth cross-over monomers together form a third hexameric nanoring;
wherein the tenth, eleventh, and twelfth dumbbell monomers and the second, third, and fourth cross-over monomers together form a fourth hexameric nanoring; and
wherein each cross-over monomer is shared by two of the hexameric rings to link the hexameric nanorings together to form the hexameric tetrahedral core.

4. The nanostructure of claim 3, wherein each dumbbell monomer comprises a helix comprising first and second ends, wherein the helix of each dumbbell monomer is capped at both ends with a kissing loop.

5. The nanostructure of claim 4, wherein the helix of each dumbbell monomer is a 15 base pair (bp) helix and each kissing loop of each dumbbell monomer is a 7 nucleotide (nt) kissing loop.

6. The nanostructure of claim 4, wherein each kissing loop has a nucleotide sequence that is unique in any one of the nanorings.

7. The nanostructure of claim 3, wherein each crossover monomer comprises first, second, third, and fourth kissing loops and first and second UA-handle three-way junctions (UAh-3WJs).

8. The nanostructure of claim 7, wherein the first UAh-3WJ is positioned symmetrically to the second UAh-3WJ in each crossover monomer.

9. The nanostructure of claim 7, wherein:
the first UAh-3WJ is positioned between a first 8 bp side helix and a first 6 bp side helix, and
the second UAh-3WJ is positioned between a second 8 bp side helix and a second 6 bp side helix.

10. The nanostructure of claim 7, wherein:
a first pair of the four kissing loops of each crossover monomer each comprise a copy of the same first nucleotide sequence, and
a second pair of the four kissing loops of each crossover monomer each comprise a copy of the same second nucleotide sequence, which is different from the first nucleotide sequence.

11. The nanostructure of claim 10, wherein:
the first pair of the four kissing loops of each crossover monomer are positioned symmetrically to one another; and
the second pair of the four kissing loops of each crossover monomer are positioned symmetrically to one another.

12. The nanostructure of claim 7, wherein the UAh-3WJs are *Escherichia coli* 23S rRNA UAh-3WJs.

13. The nanostructure of claim 7, wherein the first and second UAh-3WJs of each crossover monomer are connected by a bridge helix.

14. The nanostructure of claim 7, wherein each crossover monomer is a single RNA strand.

15. The nanostructure of claim 7, wherein:
(i) two of the four kissing loops of each crossover monomer, and one of the two UAh-3WJs of each crossover monomer, are positioned in one of the hexameric nanorings, and
(ii) the other two of the kissing loops of each crossover monomer, and the other one of the UAh-3WJs of each crossover monomer, are positioned in another one of the hexameric nanorings which is adjacent to, and directly linked to, the hexameric nanoring of (i).

16. The nanostructure of claim 3, wherein:
a first pair of the six cross-over monomers comprise copies of the same first cross-over monomer nucleotide sequence;
a second pair of the six cross-over monomers comprise copies of the same second cross-over monomer nucleotide sequence; and
a third pair of the six cross-over monomers comprise copies of the same third cross-over monomer nucleotide sequence,
wherein the first, second, and third cross-over monomer nucleotide sequences are different from one another.

17. The nanostructure of claim 3, wherein:
a first four of the twelve dumbbell monomers comprise copies of the same first dumbbell monomer nucleotide sequence;
a second four of the twelve dumbbell monomers comprise copies of the same second dumbbell monomer nucleotide sequence;
a third four of the twelve dumbbell monomers comprise copies of the same third dumbbell monomer nucleotide sequence;
wherein the first, second, and third dumbbell monomer nucleotide sequences are different from one another.

18. The nanostructure of claim 13, wherein the bridge helix connecting the first and second UAh-3WJs is a 7 bp helix.

19. The nanostructure of claim 1, wherein the core comprises four, eight, or twelve monomer arms.

20. The nanostructure of claim 19, wherein the four, eight, or twelve monomer arms are each functionalized with one or more of (a) an RNAi substrate, (b) targeting moieties, (c) imaging probes, (d) conjugated proteins, and (e) polymers.

21. The nanostructure of claim 20, wherein the RNAi substrate comprises Dicer substrate RNA (DsiRNA).

22. The nanostructure of claim 19, wherein the twelve monomer arms are each functionalized with DsiRNA.

23. The nanostructure of claim 3, wherein at least one of (a) the first, second, third, fourth, fifth, and sixth cross-over monomers, and/or at least one of (b) first, second, third, fourth, fifth, sixth, seventh, eighth, ninth, tenth, eleventh, and twelfth dumbbell monomers comprises a continuous sequence.

24. A composition comprising (a) the nanostructure of claim 1, and (b) a pharmaceutically acceptable carrier.

\* \* \* \* \*